(12) United States Patent
Yamamoto et al.

(10) Patent No.: US 9,145,267 B2
(45) Date of Patent: Sep. 29, 2015

(54) DELIVERY DEVICE

(75) Inventors: Hiroki Yamamoto, Kagawa (JP); Kenji Takeuchi, Kagawa (JP); Fumihito Kawazu, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 289 days.

(21) Appl. No.: 13/636,809

(22) PCT Filed: Mar. 17, 2011

(86) PCT No.: PCT/JP2011/056366
§ 371 (c)(1),
(2), (4) Date: Nov. 20, 2012

(87) PCT Pub. No.: WO2011/118491
PCT Pub. Date: Sep. 29, 2011

(65) Prior Publication Data
US 2013/0091998 A1    Apr. 18, 2013

(30) Foreign Application Priority Data

Mar. 26, 2010    (JP) .................................. 2010-072536

(51) Int. Cl.
*B65G 47/24*    (2006.01)
*B26D 7/06*    (2006.01)
(Continued)

(52) U.S. Cl.
CPC .......... *B65G 47/24* (2013.01); *A61F 13/15764* (2013.01); *B26D 1/40* (2013.01);
(Continued)

(58) Field of Classification Search
CPC ...... B65G 47/22; B65G 47/24; B65G 47/244; B65G 47/248; B65G 47/252; B65G 37/00; B26D 7/06; B26D 7/0633; B26D 7/0625; B26D 7/0658; B26D 7/18; B26D 7/1863; B26D 1/56; B26D 1/62; B26D 1/626; Y10T 83/2185; Y10T 83/0448; Y10T 83/0453; Y10T 83/0457; Y10T 83/0462; Y10T 83/0467; Y10T 83/0472; Y10T 83/4766; Y10T 83/4769; Y10T 83/485; Y10T 83/494; Y10T 83/483; Y10T 156/1317; Y10T 156/1322; Y10T 156/133
USPC ............... 83/152, 23–28, 321, 322, 350, 355, 83/343; 156/516, 517, 519; 198/377.01–377.08, 470.1, 471.1
See application file for complete search history.

(56) References Cited

U.S. PATENT DOCUMENTS 4,578,133 A    3/1986   Oshefsky et al.
4,608,115 A *  8/1986   Schroth et al. ................ 156/519
(Continued)

FOREIGN PATENT DOCUMENTS

CN    1917991 A     2/2007
EP    1 415 628 A1  10/2003
(Continued)

OTHER PUBLICATIONS

Chinese Office Action from corresponding Chinese Application No. 201180016095.0 dated Feb. 8, 2014 (6 pgs).
(Continued)

*Primary Examiner* — Phong Nguyen
(74) *Attorney, Agent, or Firm* — Brinks Gilson & Lione

(57) ABSTRACT

A transfer device equipped with a rotating body having multiple workpiece holding units that support a holding surface holding a continuous sheet member through suction that faces outward in the radial direction of the rotation body. Between adjacent workpiece holding units, arranged in the direction of rotation, the device is equipped with bed knives that produce single sheets by sandwiching and cutting the continuous sheet member in combination with a cutter member arranged to face the outer surface of the rotation body. The workpiece holding units pivot to follow the radial direction of rotation of the rotation body and modify the long direction face of the single sheets when the rotation of the rotation body takes the workpiece holding units past the position where the cutter member is arranged. At this time, the workpiece holding units are arranged so that part of the workpiece holding units passes over a bed knife.

2 Claims, 16 Drawing Sheets

(51) Int. Cl.
   A61F 13/15   (2006.01)
   B26D 1/40   (2006.01)
   B26D 7/01   (2006.01)
   B65H 35/08   (2006.01)
   B65H 39/14   (2006.01)
   B65H 35/00   (2006.01)
   B26D 7/00   (2006.01)

(52) U.S. Cl.
   CPC ........... *B26D 7/018* (2013.01); *B65H 35/0006* (2013.01); *B65H 35/08* (2013.01); *B65H 39/14* (2013.01); *B26D 2007/0056* (2013.01); *B65H 2301/33216* (2013.01); *B65H 2406/345* (2013.01); *B65H 2801/57* (2013.01); *Y10T 83/2185* (2015.04)

(56) References Cited

U.S. PATENT DOCUMENTS

| | | | |
|---|---|---|---|
| 6,482,278 B1 * | 11/2002 | McCabe et al. | 156/73.1 |
| 6,544,375 B1 | 4/2003 | Schmitz | |
| 6,604,623 B2 * | 8/2003 | Sumi et al. | 198/377.08 |
| 6,722,494 B2 * | 4/2004 | Nakakado | 198/792 |
| 7,587,966 B2 * | 9/2009 | Nakakado et al. | 83/37 |
| 7,987,964 B2 * | 8/2011 | McCabe | 198/471.1 |
| 2008/0196564 A1 | 8/2008 | McCabe | |
| 2010/0012458 A1 * | 1/2010 | Giuliani et al. | 198/377.04 |

FOREIGN PATENT DOCUMENTS

| | | |
|---|---|---|
| EP | 1 726 414 A1 | 1/2005 |
| JP | 60-236971 | 11/1985 |
| JP | 61-162462 | 7/1986 |
| JP | 2002-530255 A | 9/2002 |
| JP | 2003-503109 A | 1/2003 |
| JP | 2006-230438 | 9/2006 |
| JP | 2010-063716 | 3/2010 |
| WO | WO 01/00123 A1 | 1/2001 |

OTHER PUBLICATIONS

Egyptian Official Decision from corresponding Egyptian Application mailed Mar. 5, 2014 (3 pgs).
European extended Search Report in English from corresponding European Application No. 11759297.2 dated Dec. 18, 2013 (6 pgs).
Japanese Office Action from corresponding Japanese Application No. 2010-072536 dated Sep. 25, 2013 (2 pgs).
Eurasian Office Action from corresponding Eurasian Application No. 201201165/31 dated Jun. 24, 2014 (3 pgs).
International Search Report based on corresponding PCT application No. PCT/JP2011/056366 dated Jun. 21, 2011 (4 pgs).

* cited by examiner

SECTION B-B

B-B SIDE VIEW

C-C SIDE VIEW

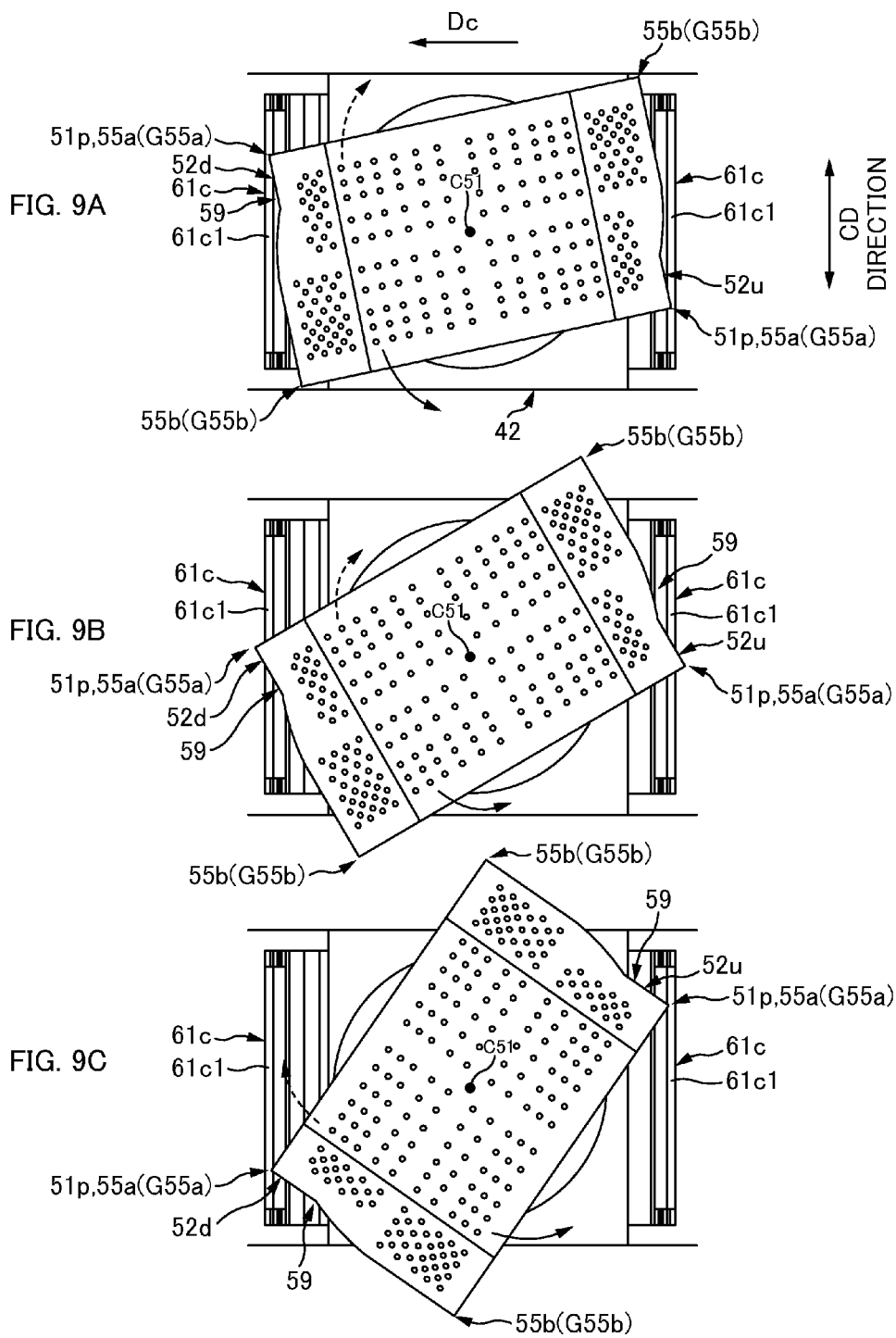

DELIVERY DEVICE

RELATED APPLICATION

The present application is a 35 U.S.C. §371 national stage filing of International Patent Application No. PCT/JP2011/056366, filed Mar. 17, 2011, to which priority is claimed under 35 U.S.C. §120 and through which priority is claimed under 35 U.S.C. §119 to Japanese Priority Patent Application No. 2010-072536, filed Mar. 26, 2010.

TECHNICAL FIELD

The present invention relates to a delivery device used for manufacturing absorbent articles such as disposable diapers and the like.

BACKGROUND ART

Conventionally, the following process is performed in a manufacturing line for absorbent articles such as disposable diapers. (For example see FIG. 2.)

First a continuously transported continuous sheet-like member 10a is received at the predetermined receiving position Qin. And while the received continuous sheet-like member 10a is transported, cut-workpieces 10 of predetermined lengths are cut and created from the continuous sheet-like member 10a.

Next, the created cut-workpiece 10 is turned around by 90 degrees to change the orientation of the longitudinal direction thereof from a flow direction of the manufacturing line (hereinafter, also referred to as the MD direction) to the width direction of the manufacturing line that is orthogonal to the flow direction (hereinafter, also referred to as the CD direction).

And lastly, this cut-workpiece 10 is transported up to the hand over position Qout and handed over at the hand over position Qout to other workpieces 20a, 24a by bonding and the like.

As an example of such process, a 90 degree drum rotating device 31 is included (for example, see FIG. 3). To be specific, this device 31 has a main rotating drum body 42 that is driven to rotate about the rotation axis C41 in the CD direction (the direction orthogonal to the plane of the paper in FIG. 3). The aforementioned receiving position Qin and the hand over position Qout are set at two locations along the rotation direction Dc. A plurality of retaining pads 51, 51 . . . for retaining by suction the continuous sheet-like member 10a transported from the upstream process are provided at a predetermined angular interval along the rotation direction Dc on the outer circumferential face of the main rotating drum body 42. Each of the retaining pads 51 are supported by the main rotating drum body 42 with the retaining surface 53 for retaining by suction in a state facing the outer side of the direction of radius of gyration Dr of the main rotating drum body 42. Additionally, a cutter roller 61a is positioned at a predetermined location in the rotation direction Dc to oppose the outer circumferential face of the main rotating drum body 42. The cutter roller 61a cooperates with the receiver 61c to sandwich and cut the continuous sheet-like member 10a. Each of the receivers 61c are provided at each parts between two retaining pads 51, 51 adjacent in the rotation direction Dc on the main rotating drum body 42. And when the receiver 61c passes the location of the cutter roller 61a by the main rotating drum body 42 driven to rotate, cut-workpieces 10 are cut and created from the continuous sheet-like member 10a for the created cut-workpieces 10 to be retained by suction by the retaining pads 51. And these retaining pads 51 are turned around by 90 degrees about the axis of revolution C51 in the direction of radius of gyration Dr before they reach the hand over position Qout and thereafter the cut-workpieces 10 are handed over to the other workpieces 20a, 24a at the hand over position Qout without changing their orientation. (PTL 1 and 2)

CITATION LIST

Patent Literature

[PTL 1]
Japanese Patent Application Laid-open Publication No. 2003-503109
[PTL 2]
Japanese Patent Application Laid-open Publication No. 2006-230438

SUMMARY OF INVENTION

Technical Problem

FIG. 14 is a schematic view of the outer circumferential face of the main rotating drum body 142 disclosed in PTL 1 with regard to the aforementioned 90 degree drum rotating device. PTL 1 discloses retaining surfaces 153 with circular contour shapes as an example of the retaining pads 151. However, with such a configuration, the retaining performance deteriorates at the end portion 10e such as the four corner parts and the like of the cut-workpiece 10 due to the circular shape causing curling, bending and the like of the end portion 10e during a 90 degree turn and the like of the retaining pad 151.

Further, when cutting and creating the cut-workpieces 10 from the continuous sheet-like member 10a with a cutter roller not shown, a wide area that cannot retain the continuous sheet-like member 10 would be created at the parts 142b (the parts 142b shaded in FIG. 14) between the receiver 161c and the retaining surface 153, in other words parts 142b proximate the receivers 161c, due to the circular shape of the retaining surface 153 similar to the case above. And as a result, the continuous sheet-like member 10 cannot be certainly retained (that is, cannot be held) by suction at the parts proximate the cutting location thus there is fear that the cutting performance will be disturbed.

Whereas, PTL 2 discloses a retaining pad 251 with a retaining surface 253 whose contour shape is approximately rectangular (see the schematic diagram of the outer circumferential face of the main rotating drum body 242 in FIG. 15A). And with this configuration, based on this approximately rectangular shape, the four corner parts of the retaining pad 251 are positioned to approximately protrude proximate the receiver 261c. Therefore, the area that cannot retain by suction the continuous sheet-like member 10a proximate the receiver 261c can be reduced, resulting to guarantee a high cutting performance. Further, based on the same approximately rectangular shape, the end portions 10e of the corner parts and the like of the cut-workpiece 10 will exhibit good retaining performance thus holding back curling, bending and the like during the 90 degree turn.

However, since the corner parts of the retaining pad 251 sticks out in four directions, there is fear that the retaining pad 251 would interfere with the receiver 261c during the 90 degree turn. In order to solve this problem, the device has been made to retract the receivers 261c inward in the direction of radius of gyration Dr of the main rotating drum body 242 during the 90 degree turn as shown in the schematic side view of FIG. 15B. However in such case, a separate driving mechanism for retracting the receivers 261c would be required making the configuration of the device complicated.

The present invention has been made in view of the conventional problems such as those mentioned above, and an object thereof is to improve the cutting performance when cutting and creating the cut-workpieces from the continuous sheet-like member as well as improve the retaining performance of the end parts of the cut-workpiece created by the cutting, while avoiding the configuration of the device becoming complicated.

Solution to Problem

In order to solve the above-described problem, a principal aspect of the invention is, a delivery device that receives a continuously transported continuous sheet-like member at a receiving position, and while the continuous sheet-like member is transported, creates cut-workpieces of predetermined lengths from the continuous sheet-like member to hand over the cut-workpieces at a hand over position, including:

a rotating body that is driven to rotate about a rotation axis and that has set the receiving position and the hand over position with an interval therebetween in a direction of rotation of the rotating body;

a plurality of workpiece retaining portions that are provided to the rotating body at a predetermined angular interval in the direction of rotation, the workpiece retaining portions being supported by the rotating body in a state where a retaining surface that retains the continuous sheet-like member by suction faces outside in a direction of radius of gyration of the rotating body;

a cutting member that is positioned at a predetermined location in the direction of rotation to oppose an outer circumferential face of the rotating body;

a receiver that is provided to the rotating body at a part between workpiece retaining portions adjacently positioned in the direction of rotation, the receiver creating the cut-workpiece on the retaining surface of the workpiece retaining portion by sandwiching and cutting the continuous sheet-like member in cooperation with the cutting member when the continuous sheet-like member passes a location in the direction of rotation where the cutting member is positioned; and a driving unit that turns around the workpiece retaining portion about an axis of revolution that is in the direction of radius of gyration, wherein the receiver is circulated by the rotating body driven to rotate, along a perfect circular orbit with the rotation axis as a center, the workpiece retaining portion that is made to pass the location where the cutting member is positioned by the rotating body driven to rotate, changes an orientation of a longitudinal direction of the cut-workpiece by turning around the axis of revolution, and therealong the workpiece retaining portion hands over the cut-workpieces when passing the hand over position, and the workpiece retaining portion is positioned so that a part of the workpiece retaining portion passes above the receiver when the workpiece retaining portion turns around the axis of revolution.

Features of the invention other than the above will become clear from the description of the present specification and the drawings attached.

Advantageous Effects of Invention

According to the present invention, it is possible to improve the cutting performance when cutting and creating the cut-workpieces from the continuous sheet-like member as well as improve the retaining performance of the end parts of the cut-workpiece created by the cutting, while avoiding the configuration of the device becoming complicated.

BRIEF DESCRIPTION OF DRAWINGS

FIG. 9A is a view showing the retaining pad 51 turning around by 90 degrees.

FIG. 9B is a view showing the retaining pad 51 turning around by 90 degrees.

FIG. 9C is a view showing the retaining pad 51 turning around by 90 degrees.

MODE FOR CARRYING OUT THE INVENTION

Figure 1A:
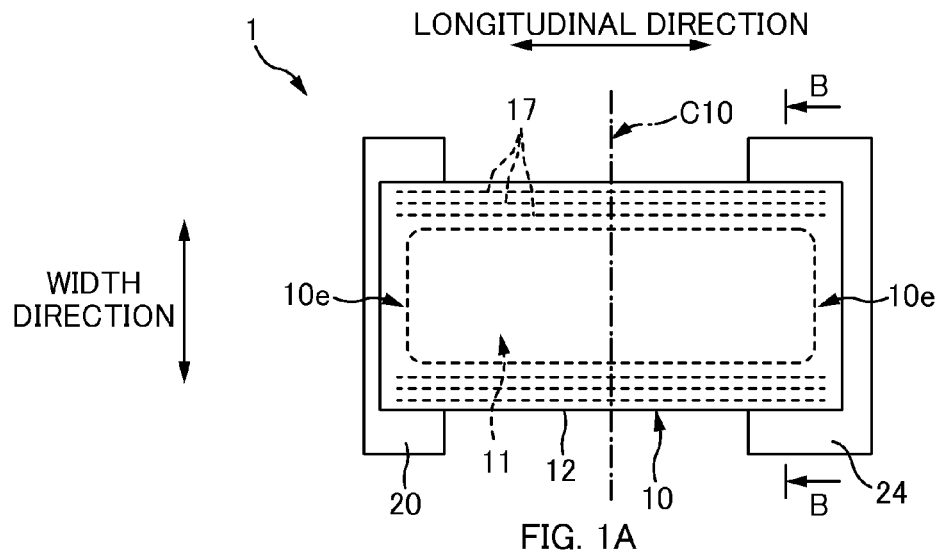
FIG. 1A is a planar view of a disposable diaper 1 in an unfolded state.

At least the following matters will be made clear from the description of the present specification with reference to the accompanying drawings.

A delivery device that receives a continuously transported continuous sheet-like member at a receiving position, and while the continuous sheet-like member is transported, creates cut-workpieces of predetermined lengths from the continuous sheet-like member to hand over the cut-workpieces at a hand over position, includes a rotating body that is driven to rotate about a rotation axis and that has set the receiving position and the hand over position with an interval therebetween in a direction of rotation of the rotating body;

a plurality of workpiece retaining portions that are provided to the rotating body at a predetermined angular interval in the direction of rotation, the workpiece retaining portions being supported by the rotating body in a state where a retaining surface that retains the continuous sheet-like member by suction faces outside in a direction of radius of gyration of the rotating body;

a cutting member that is positioned at a predetermined location in the direction of rotation to oppose an outer circumferential face of the rotating body;

a receiver that is provided to the rotating body at a part between workpiece retaining portions adjacently positioned in the direction of rotation, the receiver creating the cut-workpiece on the retaining surface of the workpiece retaining portion by sandwiching and cutting the continuous sheet-like member in cooperation with the cutting member when the continuous sheet-like member passes a location in the direction of rotation where the cutting member is positioned; and a driving unit that turns around the workpiece retaining portion about an axis of revolution that is in the direction of radius of gyration, wherein the receiver is circulated by the rotating body driven to rotate, along a perfect circular orbit with the rotation axis as a center, the workpiece retaining portion that is made to pass the location where the cutting member is positioned by the rotating body driven to rotate, changes an orientation of a longitudinal direction of the cut-workpiece by turning around the axis of revolution, and therealong the workpiece retaining portion hands over the cut-workpieces when passing the hand over position, and the workpiece retaining portion is positioned so that a part of the workpiece retaining portion passes above the receiver when the workpiece retaining portion turns around the axis of revolution.

According to such a delivery device, a part of the workpiece retaining portion is positioned to pass above the receiver during turning around. Therefore, the retaining surface of the workpiece retaining portion can be positioned to protrude to a location proximate the receiver. In other words, the end part of the workpiece retaining portion can be positioned proximate the receiver. As a result, the portion proximate the cutting location of the continuous sheet-like member can be certainly retained by suction to the retaining surface when cutting the continuous sheet-like member with the receiver and the cutting member and thereby, the cutting performance can be improved.

Further, the workpiece retaining portion is positioned so that a part of the workpiece retaining portion passes above the receiver during its turning around. In other words, the workpiece retaining portion is positioned so not to interfere with the receiver. And with such configuration, the receiver is provided to the rotating body such that the receiver is made to go around a perfect circular orbit with the rotation axis of the rotating body as the center, by the rotating body driven to rotate. That is, the receiver does not reciprocate inward and outward along the direction of radius of gyration with regard to the rotation axis of the rotating body. Thus a driving mechanism for reciprocation is not needed so that the structure of the device is avoided from becoming complicated.

Furthermore, the workpiece retaining portion is positioned so that a part of the workpiece retaining portion passes above the receiver. In this way the workpiece retaining portion can be positioned to protrude to a location proximate the receiver. Thus the end part of the cut-workpiece created by cutting with the receiver can be certainly retained. As a result, curling and bending of the end parts of the cut-workpiece can be effectively restrained when the workpiece retaining portion is turning around.

It is preferable that in the delivery device, of a face on a reverse side of the retaining surface in the workpiece retaining portion, the part that passes above the receiver when turning around the workpiece retaining portion, has a recessed portion formed.

According to such a delivery device, a recessed portion certainly allows to avoid interference with the receiver when turning around the workpiece retaining portion.

Additionally, the recessed portion is formed on a face opposite of the retaining surface. Therefore, the retaining surface can be provided to protrude proximate the location of the receiver being the location where the continuous sheet-like member is cut. And as a result, the cutting performance thereof can be improved.

It is preferable that in the delivery device, of the retaining surface of the workpiece retaining portion, the part that passes above the receiver when turning around the workpiece retaining portion has a cutout portion formed in communication with the recessed portion.

According to such a delivery device, in addition to the recessed portion formed to the face opposite the retaining surface, a cutout portion is also formed to the retaining surface in communication with the aforementioned recessed portion. Thereby, interference with the receiver when turning around the workpiece retaining portion can be certainly avoided.

Further with the aforementioned configuration, the aforementioned retaining surface can be positioned inward along the aforementioned direction of radius of gyration than the virtual straight line connecting the receivers that are adjacent to each other in the rotation direction of the aforementioned main rotating body. Therefore, the flexibility in designing the positional relationship between the retaining surface and the receiver can be enhanced. Details will be given later.

It is preferable that in the delivery device, the axis of revolution is provided at a center of a plane of the retaining surface, a contour shape of the workpiece retaining portion is in a shape having two sets of a pair of corner parts including two corner parts that are in a diagonal relationship with each other, only one pair of corner parts among the two sets of a pair of corner parts has the recessed portions and the cutout portions formed, an angle of turn of the workpiece retaining portion when changing the orientation of the longitudinal direction of the cut-workpiece is within a range of 85 to 95 degrees, and when the workpiece retaining portion returns from the hand over position to the receiving position by the rotating body driven to rotate, the workpiece retaining portion turns around in a direction opposite to that for the changing of the orientation of the cut-workpiece and by an angle same as the angle of turn so to return the orientation of the workpiece retaining portion to a state before turning around.

According to such a delivery device, a cut out portion is formed only on one pair of corner parts among the two sets of a pair of corner parts so that the retaining surface can be secured widely to improve its retaining performance.

Additionally, when the orientation of the workpiece retaining portion is returned from a turned around state by the aforementioned turn-around angle to a state before being turned around, moves along the same path on its way to and back so that the recessed portion and the cutout portion are required only at the aforementioned pair of opposing corner portions.

It is preferable that in the delivery device, the receiver is a member having a longitudinal direction oriented in parallel with the rotation axis, a contour shape of the workpiece retaining portion is a shape having four sides, two opposing sides among the four sides of the workpiece retaining portion are in a parallel state with the longitudinal direction of the receiver besides a part to which the cutout portion is formed, when the cut-workpiece is cut and created from the continuous sheet-like member, and with regard to the workpiece retaining portions adjacent across the receiver when cutting and creating the cut-workpiece, the cutout portion and the recessed portion is formed only to one corner part among the corner parts that oppose each other across the receiver.

According to such a delivery device, only one corner part among the corner parts opposing each other across the receiver has the aforementioned cutout portion and the aforementioned recessed portion formed. In other words, the cut out portions are not formed at the two side by side corners in the rotation direction across the receiver. Therefore, deterioration of the retaining performance of the continuous sheet-like member at a portion proximate the receiver due to two cut out portions provided to concentrate locally can be effectively avoided. As a result, the cutting performance of this receiver can be effectively avoided from deteriorating.

It is preferable that in the delivery device, the workpiece retaining portion includes a part that is positioned inward in the direction of radius of gyration than a virtual straight line connecting the receivers adjacent in the rotation direction, the recessed portion is formed to the part, and a bottom face of the recessed portion is located outward in the direction of radius of gyration than the virtual straight line.

According to such a delivery device, the thickness of the workpiece retaining portion can be increased inward along the aforementioned direction of radius of gyration thus realizing a workpiece retaining portion with high design flexibility.

Additionally, since the bottom face of the recessed portion is located outward along the aforementioned direction of radius of gyration than the aforementioned virtual straight line, interference between the aforementioned inwardly located portion and the receiver can be certainly avoided.

It is preferable that in the delivery device, a radius of a circular trail made by the receiver by the rotating body driven to rotate, is equal to or greater than a radius of the perfect circular orbit of the retaining surface.

According to such a delivery device, level difference and the like between the receiver at a location proximate the receiver can be restrained while the retaining surface is capable of retaining the continuous sheet-like member. As a result, the cutting performance of the cutting member can be improved.

Present Embodiment

The delivery device 31 for composite bodies 1a of continuous sheet-like members according to the present embodiment is, for example, used in a manufacturing line for disposable diapers 1.

Figure 1B:
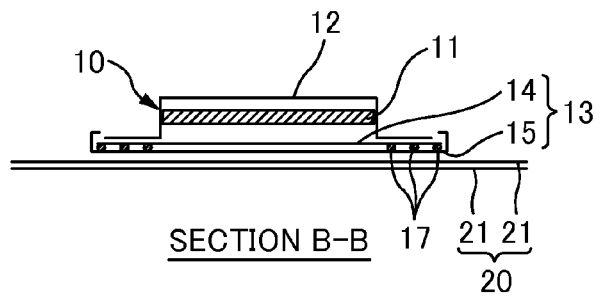
FIG. 1B is a sectional view taken along line B-B of FIG. 1A.
Figure 1C:
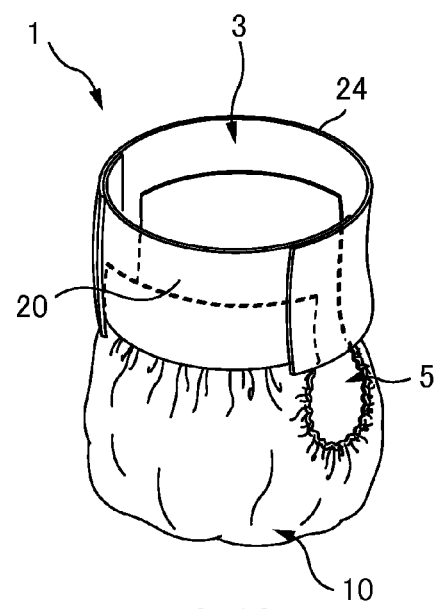
FIG. 1C is a perspective view of the diaper 1.

FIG. 1A through FIG. 1C are explanatory diagrams of disposable diapers. FIG. 1A is a planar view of a disposable diaper 1 in an unfolded state, FIG. 1B is a sectional view taken along line B-B of FIG. 1A, and FIG. 1C is a perspective view of the diaper 1.

This diaper 1 includes an abdominal side band member 20 that covers the abdominal side of the wearer, a back side band member 24 that covers the back side thereof, and a main absorbent body 10 that is set against the crotch when worn and that absorbs body fluid such as urine. In the unfolded state shown in FIG. 1A with the abdominal side band member 20 and the back side band member 24 spaced and aligned parallel with each other, the two end portions 10e, 10e in the longitudinal direction of the main absorbent body 10 are spanned therebetween and fixed thereto and its appearance configuration is in an approximately H shape seen in a planar view.

And from this state, when the main absorbent body 10 is folded into half at the center C10 in the longitudinal direction of the main absorbent body 10 and the band members 20, 24 opposing each other in the bi-fold state being fastened at portions to be in contact aside the wearer's abdomen, connects these band members 20, 24 in an annular form. In this way, a diaper 1 in a wearable state is formed with a body encircling opening 3 and a pair of leg encircling openings 5, 5 as shown in FIG. 1C.

As shown in FIGS. 1A and 1B, the main absorbent body 10 includes an absorbent body 11 made from liquid absorbent fiber such as pulp fiber to be formed into an approximately rectangular form seen in a planar view, a top sheet member 12 that covers the absorbent body 11 from the wearer's skin side, and a back side sheet member 13 that covers the absorbent body 11 from the wearer's non-skin side and also serving as the outer covering of the diaper 1. The top sheet member 12 is, for example, liquid permeable non-woven fabric whose planar size is larger than the absorbent body 11. Further the back side sheet member 13 is a liquid impermeable sheet whose planar size is larger than the absorbent body 11, and as an example, sheet 13 of a two-layer structure with a liquid impermeable leakproof sheet 14 such as polyethylene, and an outer covering sheet 15 such as non-woven fabric bonded together can be given. The backsheet member 13 and the top sheet member 12 are bonded in a frame-like form sandwiching the absorbent body 11 therebetween, at a part sticking out to the outside from the four sides of the absorbent body 11 thereby forming the absorbent body 10.

Note that, as shown in FIG. 1B, elastic members 17 such as elastic strings can be interposed and fixed in an extended state along the longitudinal direction between the leakproof sheet 14 and the cover sheet 15 at both end portions in the width direction of the backsheet member 13. In this way, elasticity is imparted to the parts around the leg encircling openings 5, 5 of the diaper 1 to form a gather portion around the legs with these elastic members 17.

The abdominal-side band 20 and the back-side band 24 are both made with, for example, elements of soft sheets such as nonwoven fabric. As shown in FIG. 1B, the band members 20 and 24 are configured with two overlapping sheets of nonwoven fabric 21, 21 and the band members 20 and 24 are respectively bonded to be fixed to the corresponding end portions 10e, 10e along the longitudinal direction of the main absorbent body 10. Further, an elastic member such as a rubber string can be fixed in a extended state to each of the band members 20 and 24 to impart elasticity to these band members 20 and 24.

Such a diaper 1 is completed by using any of the aforementioned component as base material that continuously moves along the manufacturing line, and attaching and the like various components to this base material. The delivery device 31 according to the first embodiment performs one process among these.

Figure 2:
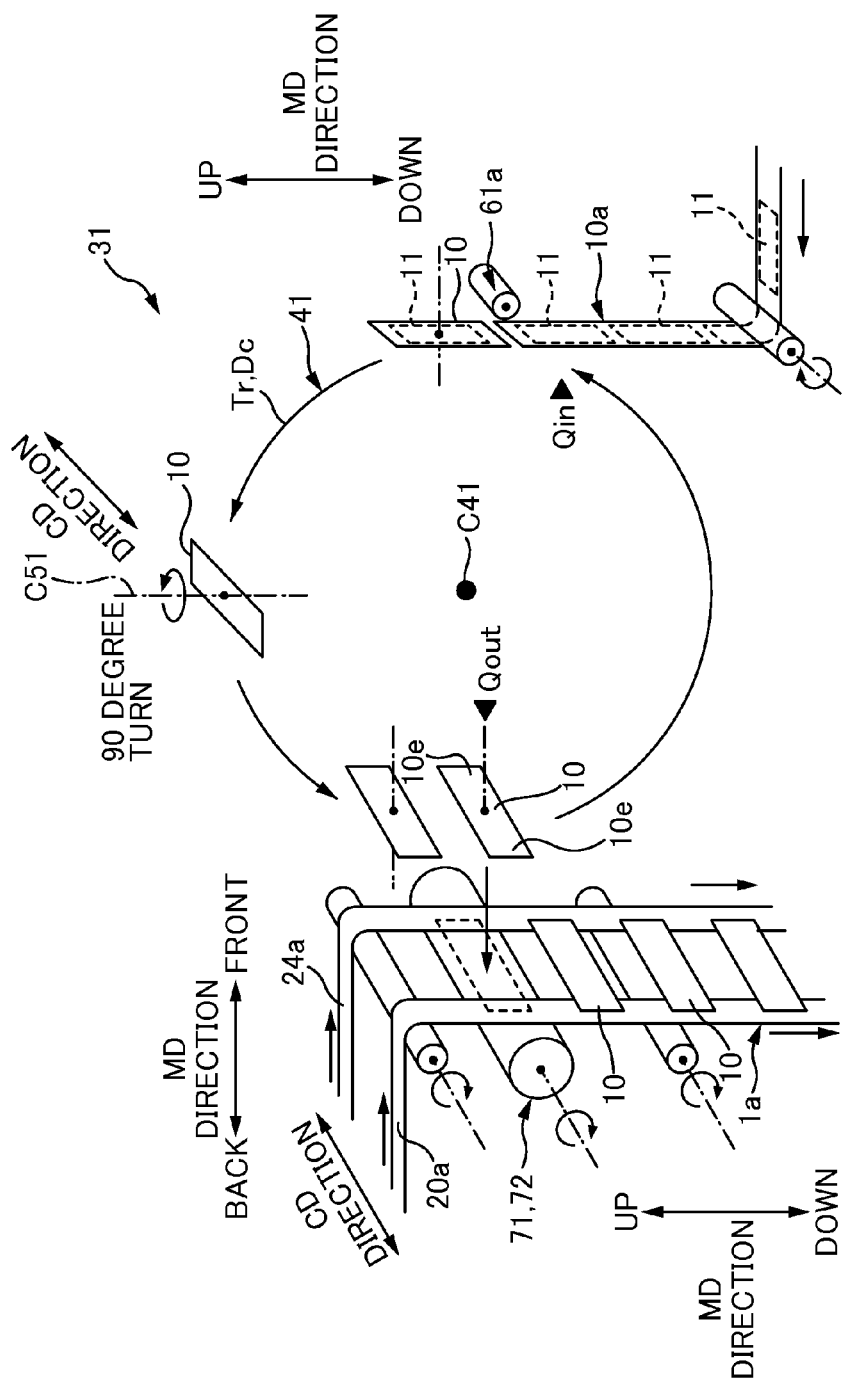
FIG. 2 is a schematic perspective diagram of a process performed by the delivery device 31 according to the present embodiment.
Figure 3:
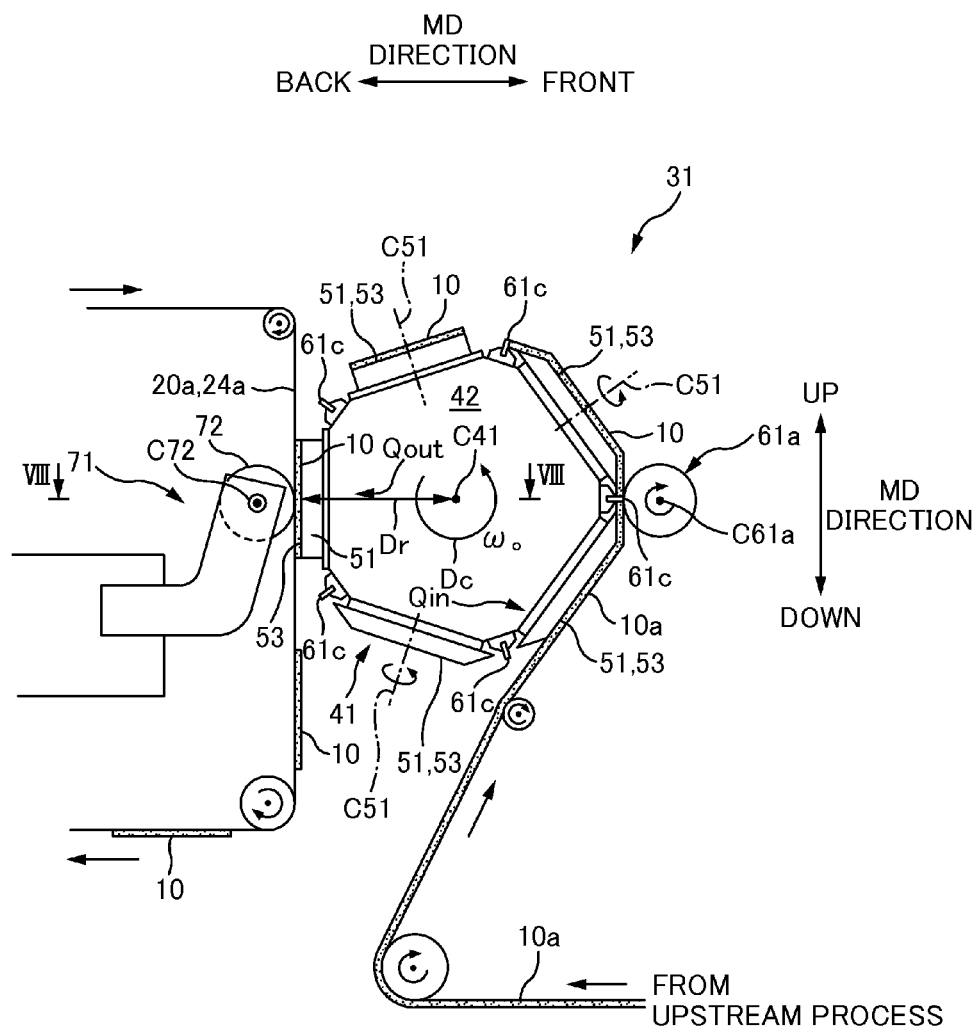
FIG. 3 is a schematic side view of the delivery device 31.

FIG. 2 is a schematic perspective diagram of a process performed by this delivery device 31. Additionally, FIG. 3 is a schematic side view of the delivery device 31.

Note that in the following description, the width direction of the delivery device 31 is referred to as also the "CD direction" and the direction orthogonal to this CD direction is referred to as also the "MD direction". In other words, the MD direction refers to any direction within a plane orthogonal to the CD direction. And in some cases, two directions orthogonal to each other within the MD direction may be respectively referred to as the "up-down direction" and the "front-back direction".

In this process, an operation of spanning the main absorbent body 10 between the pair of band members 20 and 24 to bond thereto is performed and thereby the semi-processed product 1a of the diaper 1 is made to an approximately H shape as shown in FIG. 1A.

Specifically, as shown in FIG. 2, the pair of band members 20 and 24 at the point of being supplied to the manufacturing device 31 is in a form of continuous bodies 20a, 24a in the MD direction and at the same time, continuously transported side by side in the CD direction with space therebetween. The main absorbent body 10 is also continuously transported in a form of a continuous body 10a continuous in the MD direction. In other words, the top sheet member 12 and the back side sheet member 13 that compose the main absorbent body 10 are in continuous sheet forms continuing in the longitudinal direction of the main absorbent body 10. And the top sheet member 12 and the back side sheet member 13 have interposed therebetween the absorbent body 11 while the absorbent bodies 11, 11 . . . are in a state disposed intermittently in the aforementioned longitudinal direction.

Meanwhile, the delivery device 31 has a rotating drum 41 that is driven to rotate about the rotation axis C41 in the CD direction. Firstly, at a receiving position Qin set at a predetermined location in its rotation direction Dc, the continuous body of the main absorbent body 10a is received by the outer circumferential face of the rotating drum 41 and sucked by this outer circumferential face to be retained.

Here, as an example of a cutting member, a cutter roller 61a is positioned at a predetermined location in the rotation direction Dc of the rotating drum 41. Additionally, receivers 61c, 61c . . . are set at predetermined intervals to the outer circumference of the rotating drum 41 (see FIG. 3) for receiving the cutter blades (not shown) of the cutter roller 61a. And the locations where the receivers 61c are set, are locations of the parts between the absorbent bodies 11, 11 associated with the continuous body of the main absorbent body 10a retained by the rotating drum 41.

Therefore, when the receivers 61c on the rotating drum 41 passes the location where the cutter roller 61a is placed, the continuous body of the main absorbent body 10a is divided along the CD direction at parts between the absorbent bodies 11, 11 thereby creating the main absorbent body 10 whose longitudinal direction is in the MD direction. And as shown in FIG. 2, the rotating drum 41 while its outer circumferential face retains the aforementioned main absorbent body 10, moves the main absorbent body 10 to the predetermined hand over position Qout by driving the rotating drum 41 to rotate about the rotation axis C41.

Note that this process of moving the main absorbent body 10 to the hand over position Qout includes an operation of rotating the main absorbent body 10 by 90 degrees about the center of its surface thereby changing the longitudinal direction of the main absorbent body 10 from the MD direction to the CD direction.

Meanwhile, a hand over mechanism 71 is positioned at this hand over position Qout. The hand over mechanism 71 has a transport roller 72. And the pair of continuous bodies of band members 20a and 24a side by side in the CD direction are made to come into contact with this transport roller 72 and these continuous bodies 20a and 24a are continuously transported in the MD direction. Therefore, when the main absorbent body 10 passes the aforementioned hand over position Qout by driving the rotating drum 41 to rotate, the pair of continuous bodies of band members 20a and 24a are bonded to the two end portions 10e, 10e in the longitudinal direction of the main absorbent body 10 thereby creating the semi-processed product 1a in an approximately ladder form shown in FIG. 2 being the step prior to the approximately H shape shown in the aforementioned FIG. 1A.

The processes so far are those that this delivery device 31 is in charge of. By the way, in this example, the continuous body of the main absorbent body 10a corresponds to the "continuous sheet-like member", and the main absorbent body 10 corresponds to the "cut-workpiece".

Hereinafter, description on the components 61a, 41, 71 of this delivery device 31 will be given.

<<<Cutter Roller 61a>>>

As shown in FIG. 3, the cutter roller 61a is driven to rotate about the shaft center C61a in the direction along the CD direction. And planar cutter blades (not shown) are provided in the CD direction on the outer circumferential face of the cutter roller 61a. Additionally, as mentioned above, the receivers 61c that receive these cutter blades are provided between two of the later described retaining pads 51, 51 on the outer circumferential face of the rotating drum 41.

In this way, when the receivers 61c on the rotating drum 41 passes the location where the cutter roller 61a is positioned, the cutter roller 61a driven to rotate makes the cutter blades sandwich the continuous body of the main absorbent body 10a while opposing the receivers 61c thereby cutting the continuous body of the main absorbent body 10a at the location of the border between the retaining pads 51, 51 to create the main absorbent bodies 10.

<<<Rotating Drum 41>>>

The rotating drum 41 includes a main body of the rotating drum 42 (corresponding to the rotating body) that is driven to rotate about the rotation axis C41 in the CD direction and a plurality (five in the example shown in the drawing) of retaining pads 51, 51 . . . (corresponding to the workpiece retaining portion), for retaining the main absorbent body 10, supported side by side along the rotation direction Dc at intervals of a predetermined angle (for example, intervals of 72 degrees) on the outer circumferential face of the main body of the rotating drum 42.

The main body of the rotating drum 42 is, for example, a cylindrical member whose sectional shape in the longitudinal direction is approximately a regular pentagon. And an appropriate driving source such as a motor and the like is used to drive the main body of the rotating drum 42 to rotate at, for example, a predetermined angular velocity of ω0 with the anti-clockwise direction as the direction of rotation Dc. Thereby, the retaining pads 51, 51 . . . move at a traveling speed based on the aforementioned angular velocity of ω along the orbit Tr (see FIG. 2) of a perfect circle with the aforementioned rotation axis C41 as the center. Note that as mentioned above, the shape of the orbit Tr is a perfect circle, that is, the direction of radius of gyration of the retaining pads 51 are fixed along the entire circumference of the rotation direction Dc. Therefore, the rotation of the main rotating drum body 42 is stable.

The aforementioned receiving position Qin and the hand over position Qout are set along this orbit Tr as shown in FIG. 3. Therefore, the retaining pad 51 receives the continuous body of the main absorbent body 10a transported from the upper process at the receiving position Qin and bonds the main absorbent body 10 on the retaining pad 51 to the pair of continuous bodies of band members 20a and 24a to be handed over to the hand over mechanism 71 cooperating with the transport roller 72 at the hand over position Qout. By the way, it is a matter of course that the portion subject to this bonding has adhesive provided in advance.

Figure 4A:
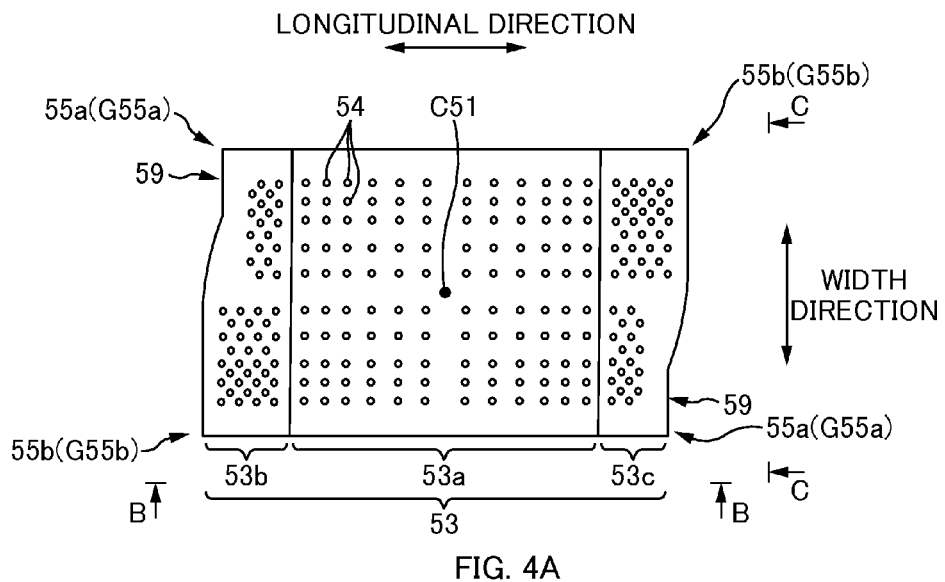
FIG. 4A is a front view (view seen from the outer side in the direction of the radius of gyration Dr) of the retaining pad 51.
Figure 4B:
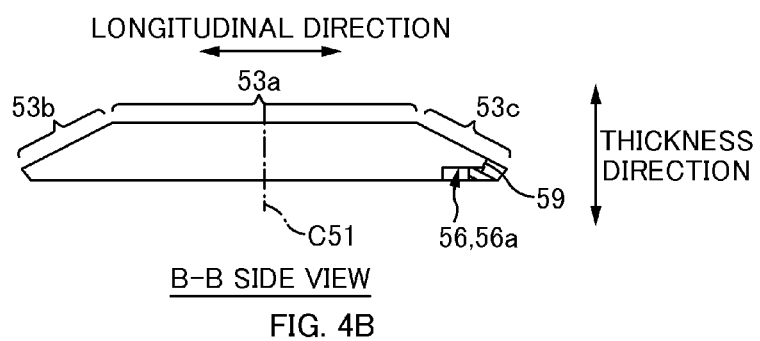
FIG. 4B is a sectional view seen from line B-B of FIG. 4A.
Figure 4C:
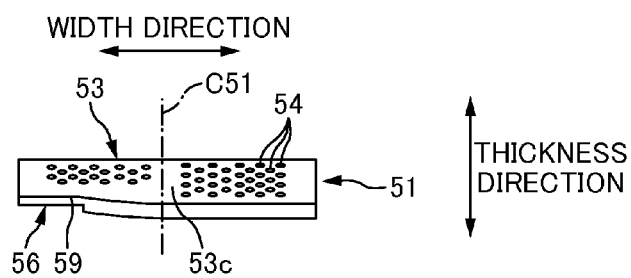
FIG. 4C is a sectional view seen from line C-C of FIG. 4A.
Figure 5A:
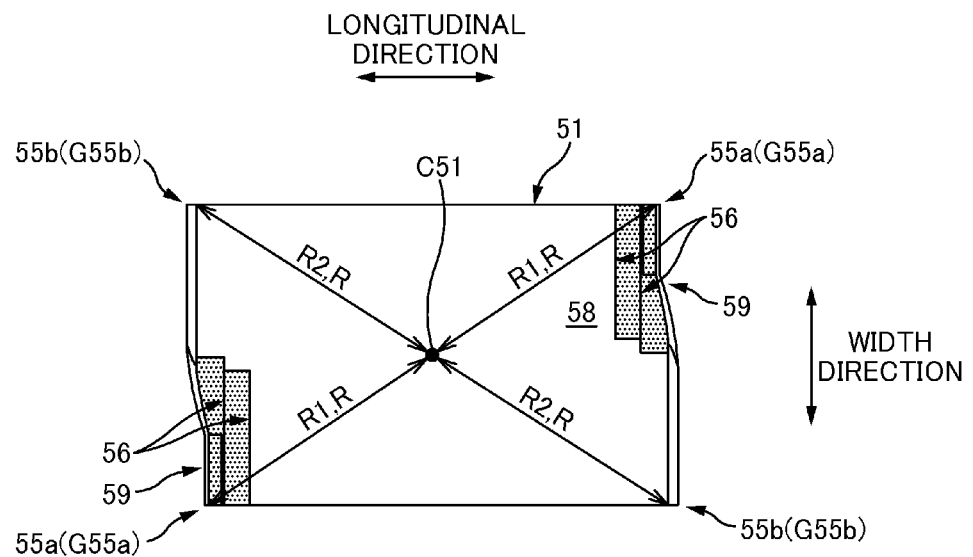
FIG. 5A is a schematic back side view of the retaining pad 51 seen from the reverse side of the retaining surface 53.
Figure 5B:
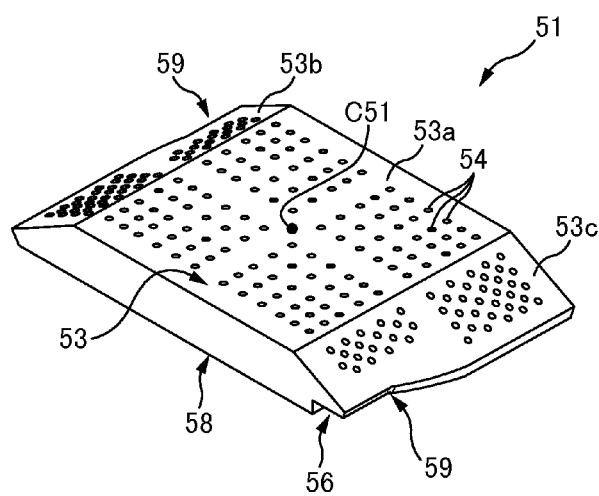
FIG. 5B is a perspective view of the retaining pad 51.

FIG. 4A is a front view (view seen from the outer side along the direction of the radius of gyration Dr) of the retaining pad 51 and FIGS. 4B and 4C are sectional views seen from line B-B and line C-C of FIG. 4A respectively. FIG. 5A is a schematic back side view of the retaining pad 51 seen from the reverse side of the retaining surface 53 and FIG. 5B is a perspective view of the retaining pad 51.

The retaining pad 51 is in an approximately rectangular plate like form having the retaining face 53 that retains the main absorbent body 10 in a state where the surfaces come into contact. And the retaining surface 53 faces the outer side in the direction of the radius of gyration Dr of the main body of the rotating body 42 while the width direction is in the direction of radius of gyration Dr as shown in FIG. 3.

As shown in FIG. 4A, the retaining surface 53 has a plurality of air intake holes 54, 54 . . . formed along the entire face thereof and theses air intake holes 54, 54 . . . are connected to a negative pressure source, not shown, through an air intake chamber or an appropriate duct and the like, not shown, inside the retaining pad 51. Therefore, a suction force for retaining the main absorbent body 10 and the like is generated on this retaining surface 53 based on air intake through the air intake holes 54, 54 . . . . This air intake operation is performed along the area between the receiving position Qin and the hand over position Qout shown in FIG. 3 and is generally not performed at areas besides this (that is, the returning area between the hand over position Qout and the receiving position Qin).

As shown in FIGS. 4A through 4C, an axis of rotation C51 is set for revolving the retaining pads 51 and this axis of rotation C51 runs through the plane center of the retaining surface 53 in a direction along the direction of the radius of gyration Dr of the rotating body 42. And the retaining pads 51 are allowed to rotate around the axis of rotation C51 by an appropriate driving source (not shown) such as a motor as the driving unit.

Therefore, as shown in FIG. 3, the retaining pads 51 rotate 90 degrees about the axis of rotation C51 after passing the location where the cutter roller 61a is positioned thereby sequentially having the longitudinal direction of the main absorbent bodies 10 changed from the MD direction to the CD direction. And after handing over the main absorbent body 10 at the hand over position Qout, the retaining pads 51 are rotated 90 degrees to receive the continuous body of the main absorbent body 10a at the receiving position Qin. And in this way, the longitudinal direction of the retaining pad 51 returns from the CD direction to the MD direction.

Note that, as shown in FIG. 4A, the retaining surface 53 is in an approximately rectangular form and also has a longitudinal direction and a width direction among which the longitudinal direction is in line with the longitudinal direction of the retaining pad 51. Additionally, as shown in FIG. 4B, the retaining surface 53 is formed to have the center part 53a in the longitudinal direction to protrude outward in a direction parallel with the aforementioned axis of rotation C51 compared with the two end parts 53b, 53c. Thereby, when this longitudinal direction is in a state facing the MD direction, as the retaining pad 51 shown on the right side in FIG. 3, the contour shape of the retaining surface 53 is in a form that is approximately along the orbit Tr of the retaining surface 53. Therefore, the speed at which each of the portions of the retaining surface 53 passes the receiving position Qin can be kept at approximately constant thereby allowing the continuous body of the main absorbent body 10a sent from the upper process to the receiving position Qin can be received in a extended state with approximately no wrinkles along the entire length in the longitudinal direction (oriented in the MD direction at the receiving position Qin) of the retaining surface 53.

Meanwhile, as shown in FIG. 4C, the retaining surface 53 is formed planar in its width direction. Therefore, the continuous body of the main absorbent body 10a can be received in an extended state with approximately no wrinkles along the entire length (entire width) in the width direction (oriented in the CD direction at the receiving position Qin) when receiving the continuous body of the main absorbent body 10a at the receiving position Qin shown in FIG. 3.

By the way, as an example of this form of the retaining surface 53 in the present embodiment, the retaining surface 53 is shown with a planar center part 53a in the longitudinal direction with the aforementioned direction of the radius of gyration Dr as the normal line and the two end parts 53b, 53c thereof with a planar inclined surface (tapered surface), however, the retaining surface 53 is not limited to such. For example, these parts 53a, 53b, 53c may be arch-shaped surfaces along the orbit Tr.

Further, as mentioned above, since the orientation of the longitudinal direction of the retaining pad 51 changes in accordance with the location where the retaining pad 51 passes along the rotation direction Dc of the retaining pad 51, the state which has the longitudinal direction of the retaining pad 51 oriented in the MD direction is called the "MD oriented position" and the state which has the longitudinal direction oriented in the CD direction is called the "CD oriented position" in the following description to clarify the directions.

Figure 6:
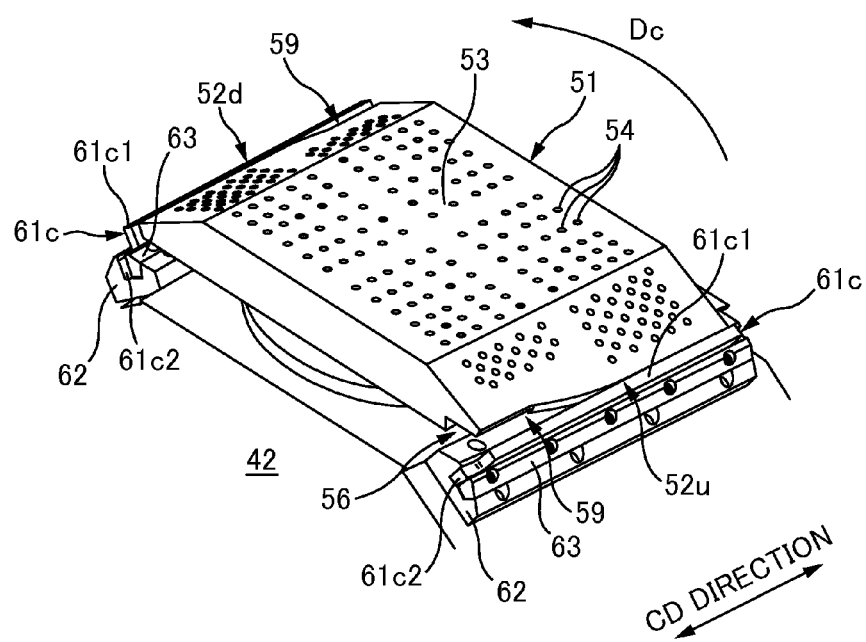
FIG. 6 is a perspective view of the receivers 61c and the retaining pad 51 positioned on the main rotating drum body 42.
Figure 7A:
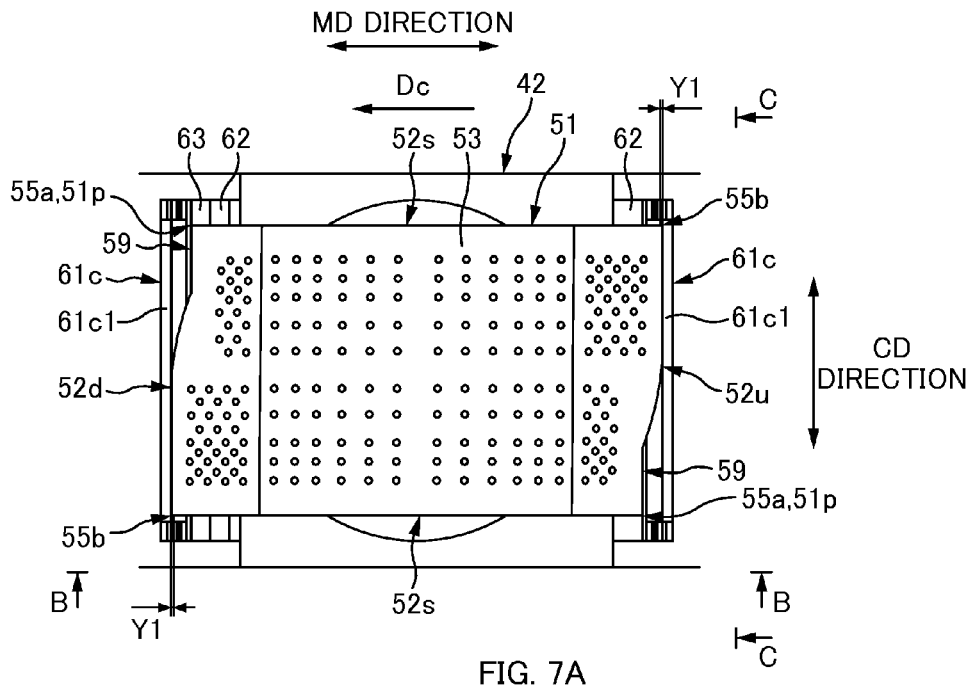
FIG. 7A is a front view of the receivers 61c and the retaining pad 51 positioned on the main rotating drum body 42.
Figure 7B:
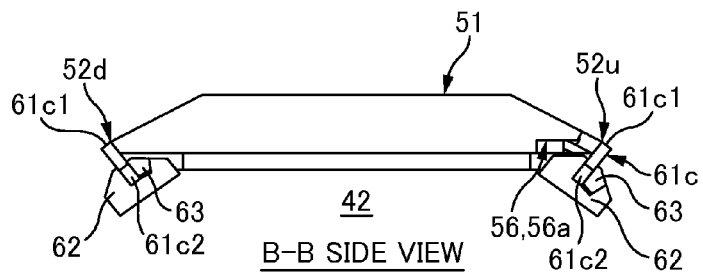
FIG. 7B is a side view seen from line B-B of FIG. 7A.
Figure 7C:
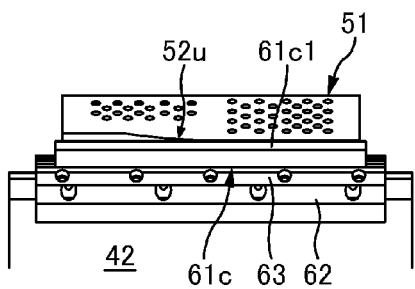
FIG. 7C is a side view seen from line C-C of FIG. 7A.

FIGS. 6 through 7C are explanatory diagrams of the receiver 61c provided to the main rotating drum body 42. FIG. 6 is a perspective view of the receivers 61c and the retaining pad 51 positioned to the main rotating drum body 42. Additionally, FIG. 7A is a front view of the receivers 61c and the retaining pad 51 positioned on the main rotating drum body 42 (view seen from the outer side along the direction of radius of gyration Dr), FIG. 7B is a side view seen from line B-B of FIG. 7A and FIG. 7C is a side view seen from line C-C of FIG. 7A.

As mentioned above, the receiver 61c is provided to a part between the retaining pads 51, 51 of the main rotating drum body 42. The receiver 61c is a planar member extending in the CD direction. And the receiver 61 includes a flat planar receiving face 61c1 that comes into contact to the cutter blade to receive the cutter blade of the cutter roller 61a during cutting, and also includes a base portion 61c2 at a location on the opposite side of the receiving face 61c1. And this base portion 61c2 is inserted into the groove of the fixing pedestal 62 fixed to the main rotating drum body 42 while an appropriate cotter member 63 fixes the base portion 61c2 in such state. In this way, the receiving face 61c1 is positioned in a state with its normal direction oriented outward along the direction of radius of gyration Dr. Therefore, the receiver 61c and the cutter roller 61a cooperate to sandwich and swiftly cut the continuous body of the main absorbent body 10a when the receiver 61c passes the location of the cutter roller 61a. By the way, it is a matter of course that the width in the CD direction of the receiving face 61c is set wider than the width of the main absorbent body 10 to be cut and is set slightly wider than the width of the retaining surface 53 of the retaining pad 51 in the examples shown in FIGS. 6 and 7A. Further, the receiver 61c is immovably fixed to the main rotating drum body 42 by the aforementioned fixing pedestal 62 and the cotter member 63. Thereby, the receiver 61c circulated by the rotating body driven to rotate, along the perfect circular orbit with the rotation axis C41 of the main rotating drum body 42 as the center.

<<<Hand Over Mechanism 71>>>

Figure 8:
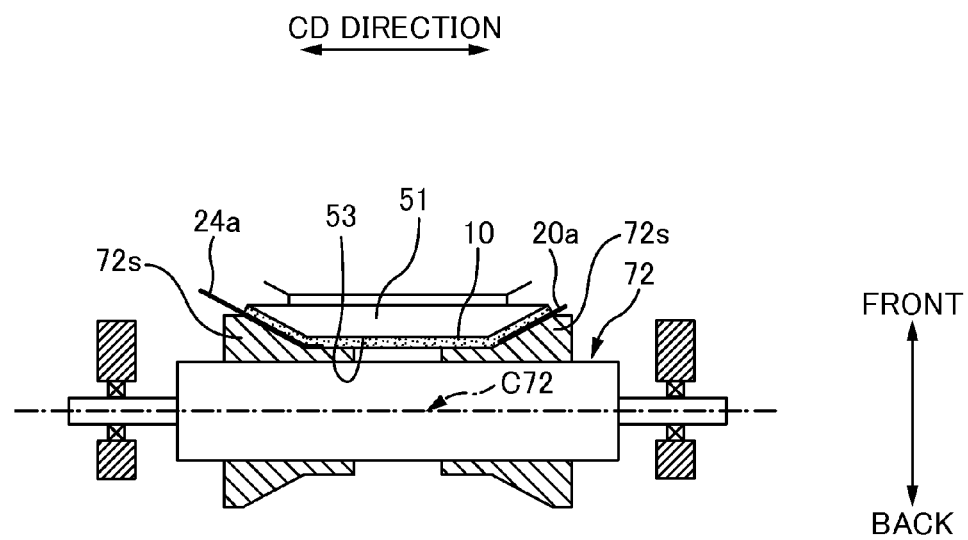
FIG. 8 is a sectional view seen from line VIII-VIII of FIG. 3.

FIG. 8 is an explanatory diagram of the hand over mechanism 71 positioned at the hand over position Qout and shows a sectional view taken along line VIII-VIII of FIG. 3.

The hand over mechanism 71 includes a transport roller 72. The transport roller 72 is a roller 72 rotatably supported about the axis C72 oriented in the CD direction. And on the circumferential face thereof, a pair of continuous bodies of band members 20a and 24a comes into contact thereto to transport the continuous bodies of band members 20a and 24a, as mentioned above. Further, a slight pushing force pushing toward the rotating drum 41 is imparted to this transport roller 72. Therefore, the main absorbent body 10 retained by the retaining pad 51 is smoothly handed over from the retaining pad 51 to the aforementioned pair of continuous bodies of band members 20a and 24a when the main absorbent body 10 passes the hand over position Qout.

By the way, as shown in FIG. 8, the contour shape of the transport roller 72 is in a drum shape with its center portion depressed in the CD direction. This is to correspond to the shape of the center portion of the retaining surface 53 of the retaining pad 51 protruding in the CD direction (FIG. 4B). And therewith, the entire length of the main absorbent body 10 along the CD direction can be certainly retained by being sandwiched approximately evenly and the like between the transport roller 72 and the retaining pad 51 passing the hand over position Qout.

Further as shown in the example of FIG. 8, the surface layer portion 72s including the outer circumferential face of the transport roller 72 can be formed with an elastic member having flexibly to be elastically deformed. Sponge-like polyurethane rubber and the like can be given as an example of the material used for this elastic member. And with such configuration, a noticeable damage on the main absorbent body 10 and the continuous bodies of band members 20a and 24a sandwiched between the retaining surface 53 and the outer circumferential face the transport roller 72 during hand over can be avoided.

<<<Cutting Performance of the Cutter Roller 61a>>>

The cutting performance when cutting the continuous body of the main absorbent body 10a with the cutter roller 61a depends on how close to the position to be cut (the location where the receiver 61c comes into contact) is retained without moving during cutting. In other words, it depends on how close to a point proximate the receiver 61c the retaining surface 53 of the retaining pad 51 is positioned to protrude.

When this protrusion is large, the end parts of the four corners of the main absorbent body 10 created by cutting with the receiver 61c, can be certainly retained by the retaining surface 53 of the retaining pad 51. And as a result, curling and bending at the end parts of the main absorbent body 10 during the 90 degree turn of the retaining pad 51 can be effectively restrained.

Therefore, in the present embodiment, the retaining pad 51 is designed so that the MD oriented position being the state of the retaining pad 51 during cutting, that is, in a state where the longitudinal direction of the retaining surface 53 is oriented in the MD direction, and the downstream edge portion 52d and the upstream edge portion 52u in the rotation direction Dc of this retaining pad 51 comes close to the respective receivers 61c, 61c opposing the upstream side and the downstream side thereof, as shown in FIGS. 6, 7A and 7B.

For example, as shown in FIG. 7A (or FIG. 10B), in the aforementioned MD oriented direction, the shorter sides 52d, 52u opposing each other among the four sides 52d, 52u, 52s, 52s of the retaining pad 51 are in parallel with the longitudinal direction of the receiver 61c besides the parts forming the later described cutout portions 59. However, in the present embodiment, the parallel parts of these shorter sides 52d, 52u and the receiver 61c are designed to be positioned proximately, so that the clearance Y1 therebetween is within the range of equal to or greater than 0.3 mm and equal to or less than 10 mm and more preferably, equal to or greater than 0.3 mm and equal to or less than 5 mm.

And here, the smaller the clearance, the more of a part 51p of the retaining pad 51 passes above the receiver 61c when turning around the retaining pad 51 by 90 degrees shown in FIGS. 9A through 9C. Specifically, more of the aforementioned downstream edge portion 52d and the upstream edge portion 52u as the aforementioned part 51, and more specifically, more of the part 51p of the predetermined area including at least two corner parts 55a, 55a in an diagonal relation among the four corner parts 55a, 55a, 55b, 55b of the retaining pad 51 passes above the receiver 61c.

Conversely, as shown in FIGS. 9A to 9C, it can be said that if the retaining pad 51 is positioned so that the aforementioned part 51p of the retaining pad 51 passes above the receiver 61c during the 90 degree turn, the retaining surface 53 of the retaining pad 51 can sufficiently retain the continuous body of the main absorbent body 10a at a location proximate the receiver 61c during cutting.

Therefore in the present embodiment, the retaining pad 51 is positioned so that the part 51p of the retaining pad 51 passes above the receiver 61c during the 90 degree turn.

Figure 10A:
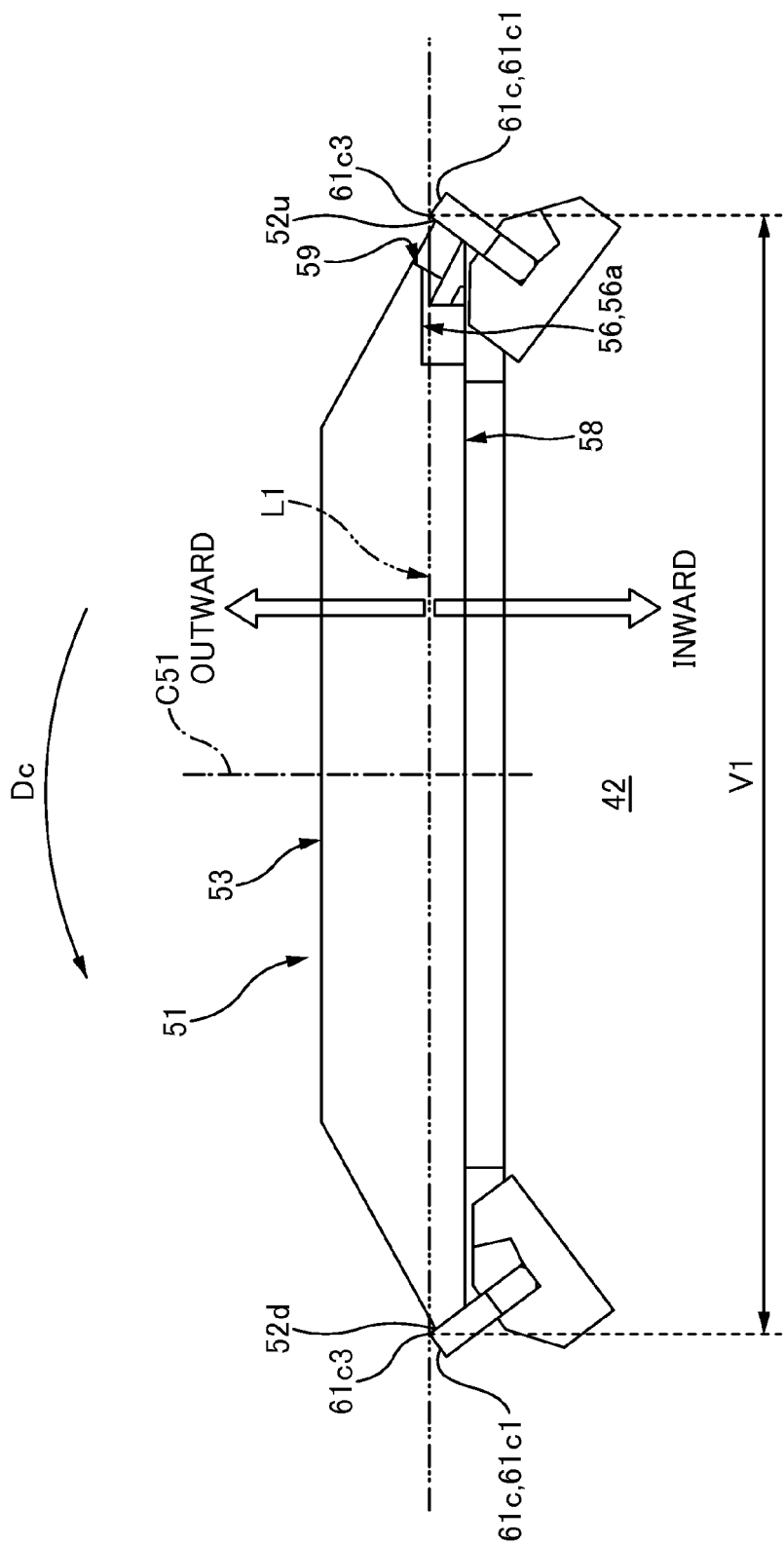
FIG. 10A is a schematic side view of the retaining pad 51.

However, when this proximate positioning is performed, the part that can pass above the receiver 61c without interference is the part which is on the outer side in the direction of radius of gyration Dr than virtual straight line L1 connecting the receivers 61c, 61c adjacent in the rotation direction Dc (more accurately, the virtual straight line L1 connecting the parts 61c3, 61c3 located outermost in the direction of the axis of revolution C51 in each of the receivers 61c) as shown in the schematic side view of the retaining pad 51 in FIG. 10A. In other words, there is a possibility that the parts on the inner side would interfere with the receiver 61c.

In detail, the retaining pad 51 turns around the axis of revolution C51 as the rotation center as described above. And this axis of revolution C51 runs through the center of the plane of the retaining surface 53 and is set along the direction of radius of gyration Dr as well. Hence, based on a geometric relation, the part that is located outward the above-described virtual straight line L1 in the direction of radius of gyration Dr would not hit the receiver 61c when turning around. However, the part that is located inward the same virtual straight line L1 in the direction of radius of gyration Dr would hit the receiver 61c, depending on the measurement of the gyration radius R.

Figure 11A:
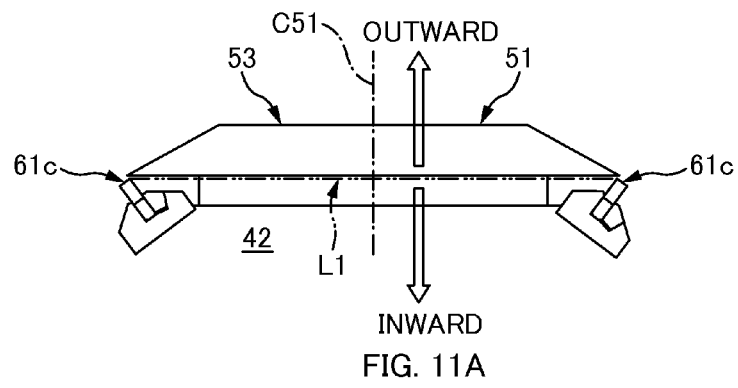
FIG. 11A is a diagram explaining a problem when all parts of the retaining pad 51 are positioned at an outer side in the direction of radius of gyration Dr than the virtual straight line L1.

Therefore, according to this idea, even if all the parts of the retaining pad 51 are configured to be located outward than the aforementioned virtual straight line L1 as in FIG. 11A, the retaining pad 51 would be able to rotate without any interference. Accordingly, a structure as shown in FIG. 11A is possible as another embodiment of the present invention.

Figure 11B:
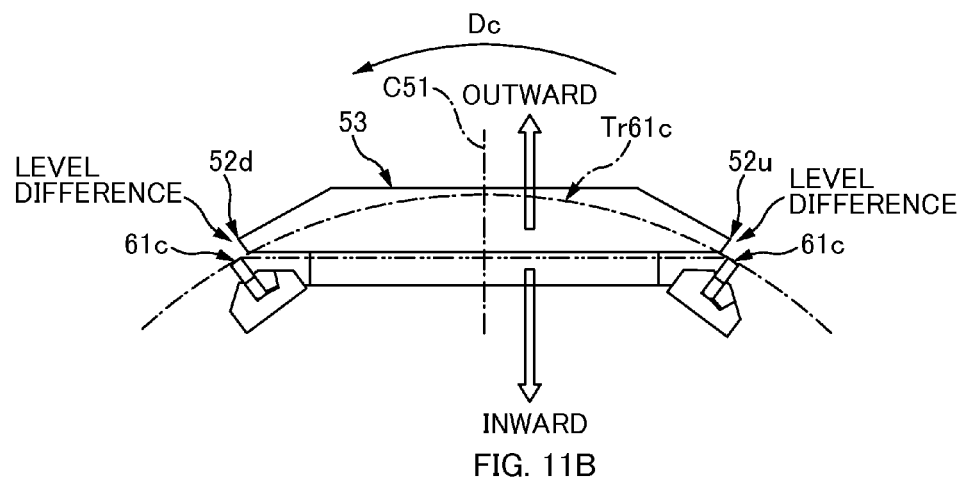
FIG. 11B is a diagram explaining a problem when all parts of the retaining pad 51 are positioned at an outer side in the direction of radius of gyration Dr than the virtual straight line L1.

However, with this structure, the retaining surface 53 would have to be designed to protrude outward in the direction of radius of gyration Dr as shown in FIG. 11B when there is a need to design the retaining pad 51 with a thicker thickness of for the purpose of providing an air intake chamber with a predetermined volume inside the retaining pad 51.

However, if it is the case, the retaining surface 53 of the retaining pad 51 would greatly jut outward from the orbit Tr61c (the circular trails made by the receiver 61c that circulates about the rotation axis C41) of the receiver 61c depending on the amount of protrusion as shown in FIG. 11B. Particularly, the thickness of the downstream edge portion 52d and the upstream edge portion 52u need to be increased when flow paths for the air intake holes 54 inside the downstream edge portion 52d and the upstream edge portion 52u in the rotation direction Dc are formed. And being the case, these edge portions 52d, 52u would jut greatly outward than the orbit Tr61c. And as a result, level difference between the receiver 61c and a part of the retaining surface 53 proximate the receiver 61c would be created whereby retaining of the continuous body of the main absorbent body 10a at the point proximate this level difference would be difficult thus there is fear of deteriorating the cutting performance.

Figure 11C:
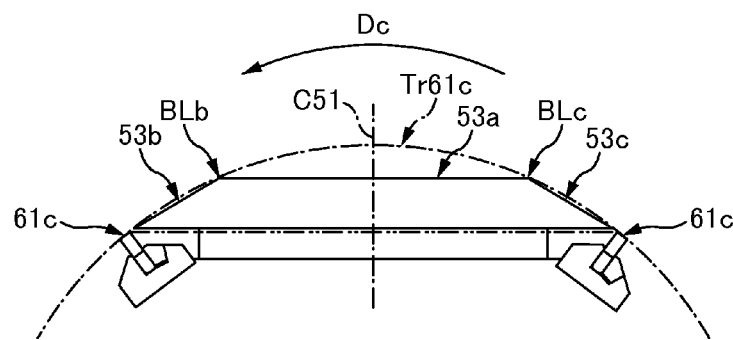
FIG. 11C is a diagram explaining a problem when all parts of the retaining pad 51 are positioned at an outer side in the direction of radius of gyration Dr than the virtual straight line L1.

In other words, restraining the irregularities of the continuous body of the main absorbent body 10a during cutting is desirable for improving the cutting performance thus the retaining performance proximate the location to be cut during the cutting would be an important factor. And from the viewpoint of improving this retaining performance, as shown in FIG. 11C, it is preferable that the end parts 53b, 53c in the rotation direction Dc of the retaining surface 53 and the border part BLb between the end part 53b and the center part 53a as well as the border part BLc between the end part 53c and the center part 53a are located to coincide with the aforementioned orbit Tr61c or located slightly inward thereof. However, with the structure shown in FIG. 11B, these parts jut outward in the direction of radius of gyration Dr than the orbit Tr61c thus resulting with a probability of bad cutting performance due to the deteriorated retaining performance.

Additionally, when synchronization of the cutter roller 61a driven to rotate is disturbed due to unexpected trouble or the like, the cutter blade, not shown, protruding from the outer circumferential face of the cutter roller 61a would hit the downstream edge portion 52d and/or the upstream edge portion 52u or the like of the retaining surface shown in FIG. 11B thus there is a risk of damaging the cutter blade and/or the retaining surface 53.

Therefore, it is preferable that the retaining pad 51 is designed to protrude inward in the aforementioned direction of radius of gyration Dr than the aforementioned virtual straight line L1 when increasing the thickness of the retaining pad 51 as shown in FIG. 10A. But in such case, there is fear of interfering with the receiver 61c.

With regard to this point, in the present embodiment, a recessed portion 56 is formed to the portion (can also be called the portion that is to pass above the receiver 61c during the 90 degree turn) that may interfere with the receiver 61c among the portions (hereinafter also called inner portions) located inward the aforementioned virtual straight line L1 in the retaining pad 51, as shown in FIG. 10A. In other words, as shown the schematic back side views in FIG. 10A and FIG. 5A, the recessed portion 56 is formed (refer to the dotted area shown in FIG. 5A) to the back face 58 (face 58 on the side that opposes the main body of the rotating drum 42) being the opposite side face 58 of the retaining surface 53 with regard to the thickness direction. And as shown in FIG. 10A (or FIG. 10B), the bottom face 56a of the recessed portion 56 is positioned outward in the direction of radius of gyration Dr than the aforementioned virtual straight line L1. Thereby, interference with the receiver 61c during the 90 degree turn is effectively avoided.

By the way, the part in this inner portion that may interfere with the receiver 61c is, as shown in FIG. 5A, the part among the aforementioned inner portion with the gyration radius R about the axis of rotation C51 that is larger than half the value of distance V1 (=V1/2, see FIG. 10A) between the receivers 61c, 61c adjacent to each other. In the example shown in FIG. 5A, the gyration radiuses R1, R2 about the axis of revolution C51 of the four corner parts 55a, 55a, 55b, 55b at the back face 58 of the retaining pad 51 becomes greater than the aforementioned value (=V1/2) so that the corner parts 55a, 55a, 55b, 55b correspond to the aforementioned portions that may interfere. Therefore, recessed portions 56 should be formed to all of these corner parts 55a, 55a, 55b, 55b in the first place and thus may be formed as in the later described example shown in FIG. 12.

However, in the present embodiment, although recessed portions 56, 56 are formed only to the two corner parts 55a, 55a among these four corner parts 55a, 55a, 55b, 55b as shown in FIG. 5A, interference with the receiver 61c is avoided by making a creative design. Details will be given on this later.

Figure 10B:
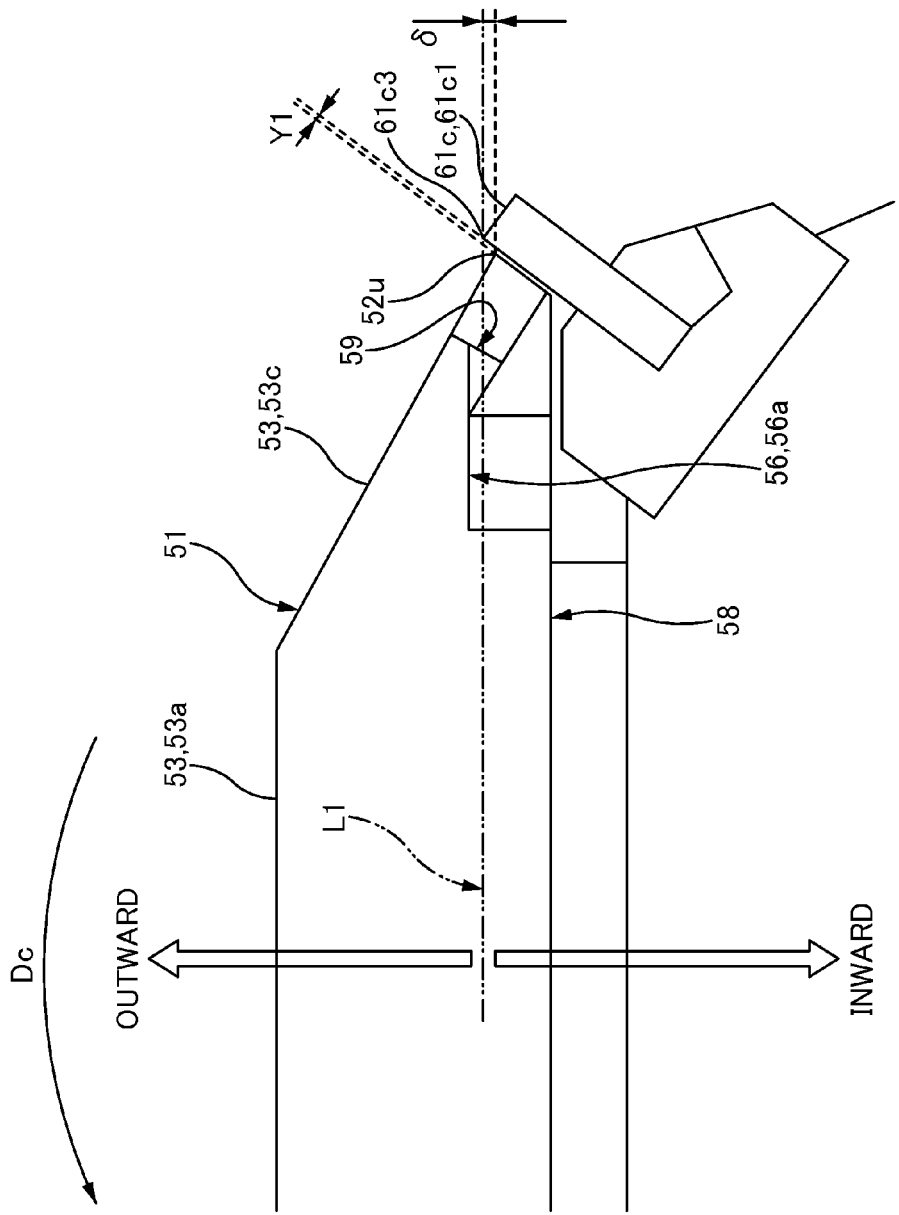
FIG. 10B is an enlarged side view of a part the retaining pad 51.

Further in the present embodiment, as shown in the enlarged side view of a part the retaining pad 51 in FIG. 10B, both the upstream edge portion 52u and the downstream edge portion 52d in the rotation direction Dc of the retaining surface 53 are located inward than the aforementioned virtual straight line L1, only by for example a slight amount 5 greater than 0 mm and equal to or less than 2 mm. Being the case, in addition to the aforementioned recessed portion 56 at the corner parts 55a, 55a at the back face 58 of the retaining pad 51, cutout portions 59 are formed in communication with the aforementioned recessed portions 56 to the parts of the retaining surface 53 that corresponds to the same corner parts 55a, 55a. And in this way, interference with the receivers 61c is avoided during the 90 degree turn of the retaining surface 53. Note that, although cutout portions 59 are already made to the corner parts 55a, 55a in FIGS. 4A to 5A and other drawings, similar to this FIG. 10B, a state without the cutout portion 59 means those same as that as the corner parts 55b in FIGS. 4A and 5B. Additionally, the cutout portion 59 is formed with an area smaller than the planar size of the recessed portion 56 so that the cutout portion 59 is not formed to protrude out from the recessed portion 56. Therefore, the area of the retaining surface 53 being reduced due to forming the cutout portion 59 can be effectively restrained. And as a result, deterioration in retaining performance due to the cutout portion 59 can be effectively avoided.

By the way, if the downstream edge portion 52d and the upstream edge portion 52u of the retaining surface 53 in FIGS. 10A and 10B are positioned outward in the direction of radius of gyration Dr than the aforementioned virtual straight line L1, these downstream edge portion 52d and upstream edge portion 52u would not interfere with the receiver 61c so that a cutout portion 59 need not be provided to the retaining surface 53.

Figure 12:
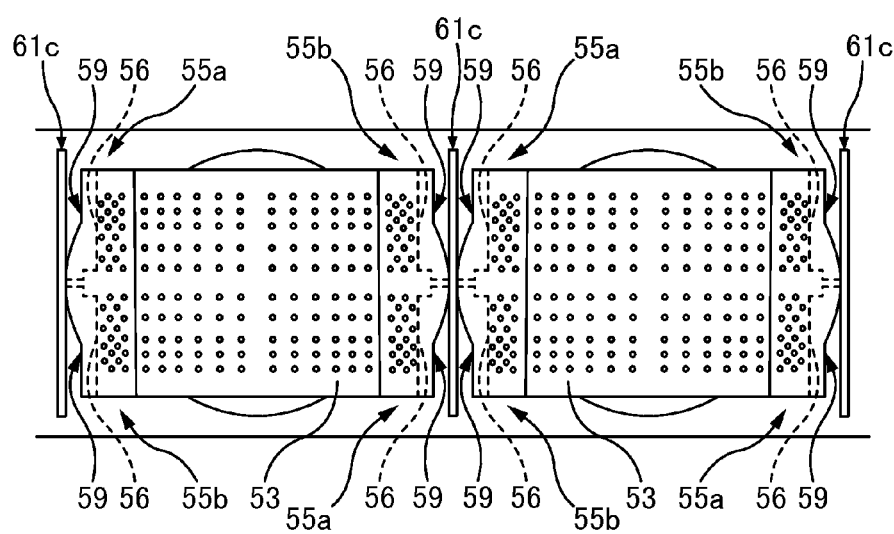
FIG. 12 is an explanatory diagram when the cutout portions 59 and the recessed portions 56 are formed at all four corner parts 55a, 55a, 55b, 55b of the retaining pad 51.

In addition, as shown in FIG. 12, the cutout portions 59 and the recessed portions 56 can be formed to all four corner parts 55a, 55a, 55b, 55b of the retaining pad 51 but it is preferable that the number of corner parts 55a, 55a, 55b, 55b with the cutout portion 59 and the recessed portion formed is small for the purpose of securing a wide area for the retaining surface 53 and from the viewpoint of securing a flow path to the air intake chamber and air intake holes 54 of the retaining pad 51.

For example, in the examples shown in FIGS. 4A and 5A, the original contour shape of the retaining surface 53 is rectangular and the retaining surface 53 has two sets of a pair of corner parts G55a (G55b) including corner part 55a (55b) and corner part 55a (55b) that are in a diagonal relationship with each other. However, only one pair of corner parts G55a among the two sets of a pair of corner parts G55a, G55b has the recessed portions 59 and the cutout portions 56 formed.

But when a cutout portion 59 or a recessed portion 56 is not formed to the pair of corner parts G55a in the above manner, the pair of corner parts G55b that is not formed the cutout portion 59 or the recessed portion 56 may hit the receiver 61c, depending on the pattern of the turn-around movement with regard to the 90 degree turn.

Therefore, in this example, the turn-around movement of the 90 degree turn of the retaining pad 51 is restricted to a predetermined pattern. That is, in the 90 degree turn-around movement, the retaining pad 51 is turned around in a pattern where the pair of corner parts G55a to which the cutout portions 59 and the recessed portions 56 are formed passes over the receiver 61c, but on the other hand the pair of corner parts G55b that are not formed these portions would not pass over the receiver 61c.

Specifically, the retaining pad makes a 90 degree turn as shown in the solid arrows lines in FIGS. 9A to 9C to orient the longitudinal direction of the main absorbent article 10 in the CD direction when the retaining pad 51 that has passed the location where the cutter roller 61a is positioned in the rotation direction Dc heads toward the hand over position Qout, but at that time, the pair of corner parts G55a having formed the cutout portions 59 and the recessed portions 56 is made to turn around so to pass above the receiver 61c (or above the receiving surface 61c1). And after handing over the main absorbent body 10 at the hand over position Qout, the retaining pad 51 when returning to the receiving position Qin makes the same 90 degree turn in the direction opposite (the direction shown in dotted arrow lines in FIGS. 9A to 9C) that of the previous 90 degree turn-around movement, that is, the turn-around movement made for orienting the direction of the main absorbent article 10 in the CD direction. Thereby, the corner parts 55a, 55a to which the cutout portions 59 and the recessed portions 56 are made passes above the receiver 61c (or above the receiving surface 61c1) during this turn-around so that the retaining pad 51 is swiftly returned to the state before turning around in a direction with its longitudinal direction oriented in the rotation direction Dc without the retaining pad 51 and the receiver 61c interfering each other at all.

By the way as shown in FIG. 12, there is no restriction to the above described turn-around movement pattern when the cutout portions 59 and the recessed portions 56 are formed to all four corner parts 55a, 55a, 55b, 55b of the retaining pad 51. That is, the turn-around movements of the retaining pad 51 being the 90 degree turn made while the retaining pad 51 moves from the location where the cutter roller 61a is positioned to the hand over position Qout, and the 90 degree turn while the retaining pad 51 returns from the hand over position Qout to the receiving position Qin, can be made in the same direction. In other words, the retaining pad 51 can make a 360-degree turn about the axis of revolution C51.

Note that, this turn-around movement pattern of a 90 degree turn can be easily realized by a forward reverse control of the motor that drives the retaining pad 51 to turn around.

Figure 13A:
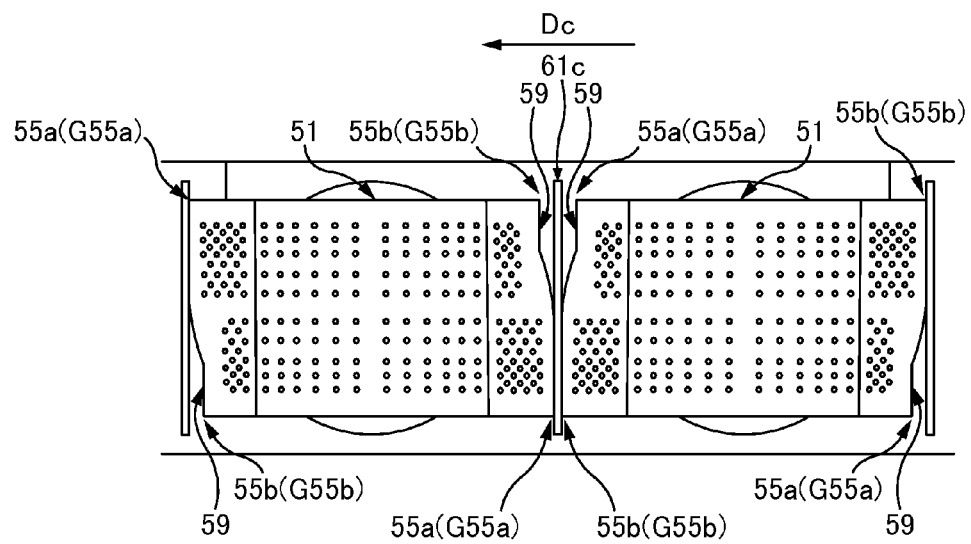
FIG. 13A is a diagram for explaining which corners 55a, 55b should have the cutout portions 59 and the recessed portions 56 formed.
Figure 13B:
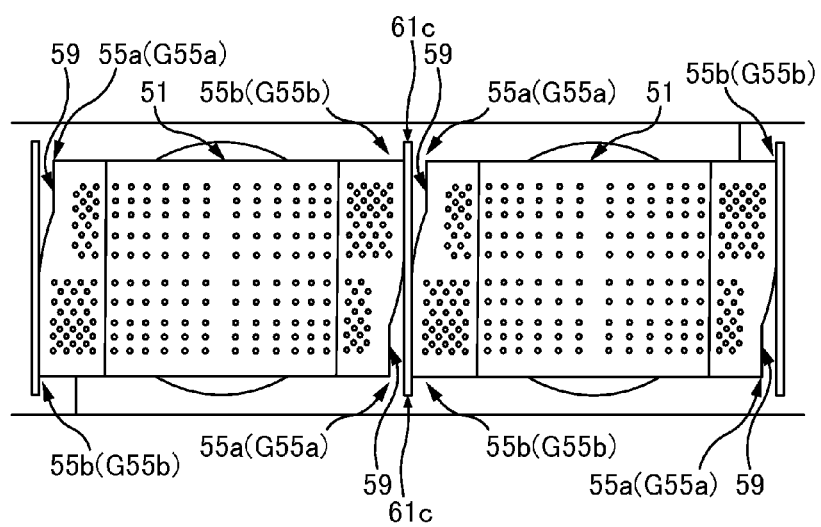
FIG. 13B is a diagram for explaining which corners 55a, 55b should have the cutout portions 59 and the recessed portions 56 formed.
Figure 14:
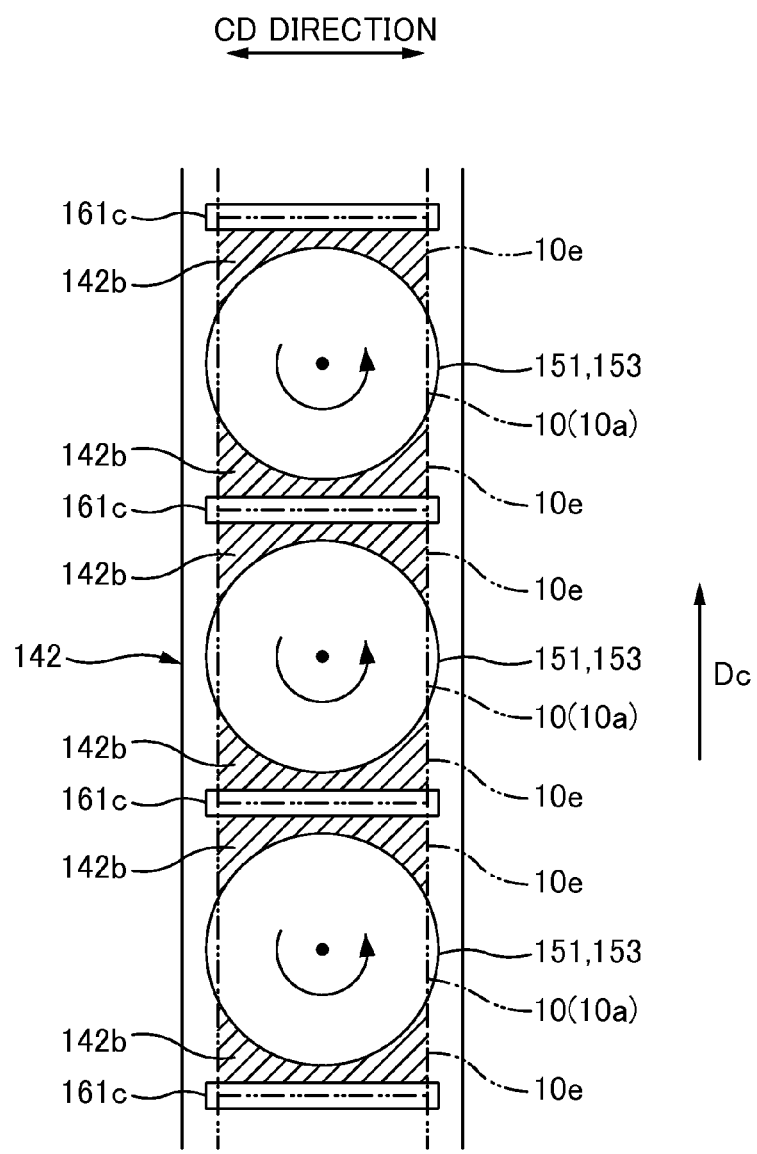
FIG. 14 is a schematic diagram of the outer circumferential face of a conventional main rotating drum body 142.
Figure 15A:
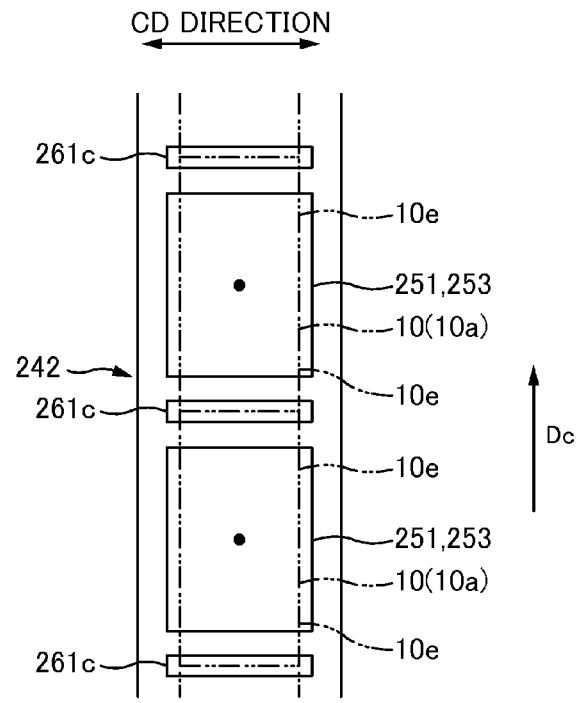
FIG. 15A is a schematic diagram of the outer circumferential face of the conventional main rotating drum body 242.
Figure 15B:
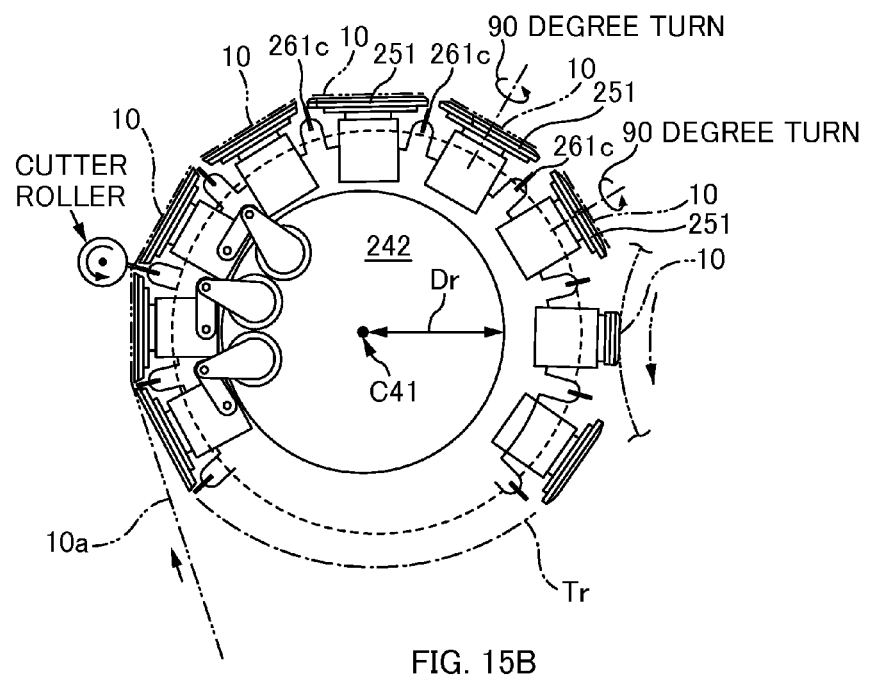
FIG. 15B is a schematic side diagram of a device including the main rotating drum body 242.

By the way as shown in FIGS. 13A and 13B, if to mention which corner parts 55a, 55b is preferred to have the cutout portions 59 and the recessed portions 56 formed among the eight corner parts 55a, 55a, ..., 55b, 55b, ... that are included in the retaining pads 51, 51 adjacent to each other across the receiver 61c during cutting, it is preferable that the cutout portion 59 and the recessed portion 56 are formed only to one corner part 55a among the corner parts 55a, 55b that oppose each other in the rotation direction Dc across the receiver 61c, as shown in FIG. 13B. In this way, the cutout portions 59, 59 concentrating at a part proximate the receiver 61c between the corner parts 55a, 55b as in FIG. 13A can be avoided as in the example shown in FIG. 13B. And as a result, the deterioration in the retaining performance by suction of the continuous body of the main absorbent body 10a can be effectively restrained thus improving the cutting performance when cutting the continuous body of the main absorbent body 10a in the example shown in FIG. 13B.

By the way, the positional relation with regard to the cutout portions 59 and the recessed portions 56 shown in FIG. 13B can be expressed in the following way. The positional relationship of the pair of corner parts G55a formed to the retaining pads 51 with the cutout portions 59 and the recessed portions 56 are the same with regard to of all of the retaining pads 51, 51 ... equipped to the main body of the rotating drum 42.

Other Embodiments

Hereinabove, description was given of embodiments of the present invention, however, the present invention is not limited to such embodiments and may be modified in the following ways.

In the aforementioned embodiment, the retaining pad 51 as the workpiece retaining portion was turned around the axis of revolution by 90 degrees to change the orientation of the longitudinal direction of the main absorbent body 10 as the cut-workpiece from the MD direction to the CD direction, however, the turn-around angle is not limited to such as long as the angle is within the range of 85 to 95 degrees.

In the aforementioned embodiment, as explained above with reference to FIG. 10B, the upstream edge portion 52u and the downstream edge portion 52d of the retaining surface 53 was positioned inward the direction of radius of gyration Dr than the virtual straight line L1 by a slight amount δ, however, the positioning is not limited to such. For example, the upstream edge portion 52u and the downstream edge portion 52d may be located on the virtual straight line L1, or may be located slightly outward by an amount of δ2 (not shown) than the virtual straight line L1. Note that, in this case, the value to which the slight amount δ2 is set is selected from the range of 0 mm to 2 mm. In addition, at least the cutter blade of the cutter roller 61a would be formed to protrude out from the outer circumferential face corresponding to this slight amount δ2.

REFERENCE SIGNS LIST 1 disposable diaper, 10 main absorbent body (cut-workpiece), 10a continuous body of main absorbent body (continuous sheet-like member), 10e end portion, 11 absorbent body, 12 top sheet member, 13 back side sheet member, 14 leakproof sheet, 15 outer covering sheet, 17 elastic member, 20 abdominal-side band member, 20a continuous body of abdominal-side band member, 21 nonwoven fabric, 24 back side band member, 24a continuous body of back side band member, 31 delivery device, 41 rotating drum, main body of the rotating drum (rotating body), 51 retaining pad (workpiece retaining portion), 51p a part, 52d downstream edge portion (side), 52u upstream edge portion (side), 52s side, 52s side, 53 retaining surface, 53a center part, 53b end part, 53c end part, 54 air intake hole, 55a corner part, 55b corner part, 56 recessed portion, 56a bottom face, 58 back face, 59 cutout portion, 61a cutter roller (cutting member), 61c receiver, 61c1 receiving surface, 61c2 base portion, 61c3 part, fixing pedestal, 63 cotter member, 71 hand over mechanism, 72 transport roller, 72s surface layer portion, G55a pair of corner parts, G55b pair of corner parts, L1 virtual straight line, BLb border part, BLc border part, C10 center, C41 rotation axis, C51 axis of revolution, C61a shaft center, C72 axis center, Qin receiving position, Qout hand over position, Tr orbit, Tr61C orbit, Dc rotation direction, Dr direction of radius of gyration, R gyration radius, R1 gyration radius, V1 distance, Y1 clearance

The invention claimed is:

1. A delivery device that receives a continuously transported continuous sheet member at a receiving position, and while the continuous sheet member is transported, creates cut-workpieces of predetermined lengths from the continuous sheet member to hand over the cut-workpieces at a hand over position, comprising:
    a rotating body that is driven to rotate about a rotation axis and the receiving position and the hand over position are set along the direction of rotation of the rotating body;
    a plurality of workpiece retaining portions that are provided to the rotating body at a predetermined angular interval in the direction of rotation, the workpiece retaining portions being supported by the rotating body in a state where a retaining surface that retains the continuous sheet member by suction faces outside in a direction of radius of gyration of the rotating body;
    a cutting member that is positioned at a predetermined location in the direction of rotation to oppose an outer circumferential face of the rotating body;
    a receiver that is provided to the rotating body at a part between workpiece retaining portions adjacently positioned in the direction of rotation, the receiver creating the cut-workpiece on the retaining surface of the workpiece retaining portion by sandwiching and cutting the continuous sheet member in cooperation with the cutting member when the continuous sheet member passes a location in the direction of rotation where the cutting member is positioned; and
    a driving unit that turns around the workpiece retaining portion about an axis of revolution that is in the direction of radius of gyration, wherein
    the receiver is circulated by the rotating body driven to rotate, along a perfect circular orbit with the rotation axis as a center,
    the workpiece retaining portion that is made to pass the location where the cutting member is positioned by the rotating body driven to rotate, changes an orientation of a longitudinal direction of the cut-workpiece by turning around the axis of revolution, and therealong the workpiece retaining portion hands over the cut-workpieces when passing the hand over position,
    the workpiece retaining portion is positioned so that a part of the workpiece retaining portion passes above the receiver when the workpiece retaining portion turns around the axis of revolution,
    a part of a face on a reverse side of the retaining surface in the workpiece retaining portion that passes above the receiver when turning around the workpiece retaining portion includes a recessed portion,
    a part of the retaining surface of the workpiece retaining portion that passes above the receiver when turning around the workpiece retaining portion has a cutout portion formed in communication with the recessed portion,
    the axis of revolution is provided at a center of a plane of the retaining surface,
    a contour shape of the workpiece retaining portion is in a shape having two sets of a pair of corner parts including two corner parts that are in a diagonal relationship with each other,
    only one pair of corner parts among the two sets of a pair of corner parts has the recessed portions and the cutout portions formed,
    an angle of turn of the workpiece retaining portion when changing the orientation of the longitudinal direction of the cut-workpiece is within a range of 85 to 95 degrees, and
    when the workpiece retaining portion returns from the hand over position to the receiving position by the rotating body driven to rotate, the workpiece retaining portion turns around in a direction opposite to that for the changing of the orientation of the cut-workpiece and by an angle same as the angle of turn so to return the orientation of the workpiece retaining portion to a state before turning around.

2. The delivery device according to claim 1, wherein
    the receiver is a member having a longitudinal direction oriented in parallel with the rotation axis,
    a contour shape of the workpiece retaining portion is a shape having four sides,
    two opposing sides among the four sides of the workpiece retaining portion are in a parallel state with the longitudinal direction of the receiver besides a part to which the cutout portion is formed, when the cut-workpiece is cut and created from the continuous sheet member, and
    with regard to the workpiece retaining portions adjacent across the receiver when cutting and creating the cut-workpiece, the cutout portion and the recessed portion is formed only to one corner part among the corner parts that oppose each other across the receiver.

* * * * *